United States Patent
Deshmukh et al.

(10) Patent No.: US 10,947,307 B2
(45) Date of Patent: Mar. 16, 2021

(54) ANTIBODY FORMULATIONS

(71) Applicant: GENENTECH, INC., South San Francisco, CA (US)

(72) Inventors: Ajay Deshmukh, San Francisco, CA (US); Joumana Zeid, Oakland, CA (US); Thomas M. Scherer, San Carlos, CA (US)

(73) Assignee: Genentech, Inc, South San Francisco, CA (US)

( * ) Notice: Subject to any disclaimer, the term of this patent is extended or adjusted under 35 U.S.C. 154(b) by 126 days.

(21) Appl. No.: 16/002,932

(22) Filed: Jun. 7, 2018

(65) Prior Publication Data

US 2019/0002552 A1     Jan. 3, 2019

Related U.S. Application Data

(60) Division of application No. 14/259,882, filed on Apr. 23, 2014, now Pat. No. 10,000,562, which is a continuation of application No. PCT/US2012/062572, filed on Oct. 30, 2012.

(60) Provisional application No. 61/553,916, filed on Oct. 31, 2011.

(51) Int. Cl.

| | |
|---|---|
| C07K 16/24 | (2006.01) |
| A61K 39/395 | (2006.01) |
| A61K 9/00 | (2006.01) |
| A61P 37/08 | (2006.01) |
| A61K 47/18 | (2017.01) |
| A61K 47/26 | (2006.01) |
| A61M 5/24 | (2006.01) |

(52) U.S. Cl.
CPC .......... *C07K 16/244* (2013.01); *A61K 9/0019* (2013.01); *A61K 47/183* (2013.01); *A61K 47/26* (2013.01); *A61M 5/24* (2013.01); *A61P 37/08* (2018.01); *A61K 39/39591* (2013.01); *C07K 2317/24* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 7,758,860 B2 | 7/2010 | Warne et al. | |
| 8,142,776 B2 | 3/2012 | Liu et al. | |
| 2005/0118169 A1 | 6/2005 | Bartke et al. | |
| 2007/0172479 A1 | 7/2007 | Warne et al. | |
| 2007/0253951 A1 | 11/2007 | Ng et al. | |
| 2008/0008648 A1 | 1/2008 | Fung et al. | |
| 2008/0160014 A1 | 7/2008 | Warne et al. | |
| 2008/0267959 A1 | 10/2008 | Campbell et al. | |
| 2009/0060906 A1 | 3/2009 | Barry et al. | |
| 2009/0214523 A1 | 8/2009 | Fung et al. | |
| 2010/0015157 A1 | 1/2010 | Andya et al. | |
| 2010/0239567 A1 | 9/2010 | Esue | |

FOREIGN PATENT DOCUMENTS

| | | |
|---|---|---|
| WO | WO 2002012501 A2 | 2/2002 |
| WO | WO 2002012501 A3 | 2/2002 |
| WO | WO 2002030463 A2 | 4/2002 |
| WO | WO 2002030463 A3 | 4/2002 |
| WO | WO 2003105894 A1 | 12/2003 |
| WO | WO 2003106644 A2 | 12/2003 |
| WO | WO 2003106644 A3 | 12/2003 |
| WO | WO 2004075918 A1 | 9/2004 |
| WO | WO 2004091658 A1 | 10/2004 |
| WO | WO 2005062967 A2 | 7/2005 |
| WO | WO 2005062967 A3 | 7/2005 |
| WO | WO 2006044908 A2 | 4/2006 |
| WO | WO 2006044908 A3 | 4/2006 |
| WO | WO 2006065746 A2 | 6/2006 |
| WO | WO 2006065746 A3 | 6/2006 |
| WO | WO 2007036745 A2 | 4/2007 |
| WO | WO 2007036745 A3 | 4/2007 |
| WO | WO 2007076062 A2 | 7/2007 |
| WO | WO 2007076062 A3 | 7/2007 |
| WO | WO 2008086395 A2 | 7/2008 |
| WO | WO 2008086395 A3 | 7/2008 |
| WO | WO 2010039851 A1 | 4/2010 |
| WO | WO 2010039851 A9 | 4/2010 |
| WO | WO 2010063493 A1 | 6/2010 |
| WO | WO 2010102241 A1 | 9/2010 |
| WO | WO 2011104381 A2 | 9/2011 |
| WO | WO 2011104381 A3 | 9/2011 |
| WO | WO 2011119487 A2 | 9/2011 |
| WO | WO 2011119487 A3 | 9/2011 |
| WO | WO 2011139718 A1 | 11/2011 |
| WO | WO 2012151199 A1 | 11/2012 |
| WO | WO 2013066866 A1 | 5/2013 |

OTHER PUBLICATIONS

"Prefilled syringes: the container of choice for today's injectables", OnDrugDelivery, 2008, pp. 1-44.*
Australian Public Assessment Report for Golimumab, Submission No. PM-2008-1811-3, Sponsor: Schering-Plough Pty Ltd, 80 pages (Dec. 2009).
Akbari et al., "Essential role of NKT cells producing IL-4 and IL-13 in the development of allergen-induced airway hyperreactivity" Nature Medicine 9(5):582-588 ( 2003).
Akers et al., "Formulation development of protein dosage forms" Pharmaceutical Biotechnol 14:47-127 (Jan. 1, 2002).
Arguelles et al., "Inflammatory bronchial polyps associated with asthma" Arch Intern Med 143(3):570-571 (1983).
Asherie et al., "Protein crystallization and phase diagrams" Methods 34:266-272 ( 2004).
Assarian et al., "Inflammatory fibroid polyp of the ileum," Hum Pathol 16(3):311-312 (1985).

(Continued)

*Primary Examiner* — Bridget E Bunner
*Assistant Examiner* — Fozia Hamud
(74) *Attorney, Agent, or Firm* — Xiaoguang Gao

(57) ABSTRACT

Formulations comprising an anti-IL-13 antibody are provided, including pharmaceutical formulations and methods of using such formulations.

18 Claims, 11 Drawing Sheets

Specification includes a Sequence Listing.

(56) References Cited

OTHER PUBLICATIONS

Atanes et al., "Idiopathic eosinophilic synovitis. Case report and review of the literature" Scand J Rheumatol 25(3):183-185 ( 1996).
Bachert et al., "Total and specific IgE in nasal polyps is related to local eosinophilic inflammation" J Allergy Clin Immunol 107:607-614 ( 2001).
Bettelheim et al., "Effect of change in concentration upon lens turbidity as predicted by the random fluctuation theory" Biophys J 41:29-33 (Jan. 1983).
Bouros et al., "Histopathologic subsets of fibrosing alveolitis in patients with systemic sclerosis and their relationship to outcome," Am J Respir Crit Care Med 165:1581-1586 (2002).
Breen, E.D. et al., "Effect of Moisture on the Stability of a Lyophilized Humanized Monoclonal Antibody Formulation" Pharm Res 18(9):1345-1353 (Sep. 2001).
Burckbuchler et al., "Rheological and syringeability properties of highly concentrated human polyclonal immunoglobulin solutions" Eur J Pharmaceutics Biopharmaceutics 76:351-356 ( 2010).
Carpenter et al., "Rational Design of Stable Lyophilized Protein Formulations: Some Practical Advice" Pharm Res 14(8):969-975 ( 1997).
Chang et al., "Mechanisms of protein stabilization in the solid state" J Pharm Sci 98(9):2886-2908.
Chen et al., "Eosinophilic vasculitis in connective tissue disease," J Am Acad Dermatol, 35(2 Pt 1), 173-182 (1996).
Chen et al., "Influence of histidine on the stability and physical properties of a fully human antibody in aqueous and solid forms" Pharm Res 20(12):1952-1960 (Dec. 2003).
Chi et al., "Physical stability of proteins in aqueous solution: mechanism and driving forces in nonnative protein aggregation" Pharm Res 20(9):1325-1336 (Sep. 2003).
Chi et al., "Roles of conformational stability and colloidal stability in the aggregation of recombinant human granulocyte colony-stimulating factor" Protein Sci 12:903-913 ( 2003).
Cleland et al., "The Development of Stable Protein Formulations: A Close Look at Protein Aggregation, Deamidation, and Oxidation" Crit Rev Ther Drug 10(4):307-377 ( 1993).
Connolly et al., "Diffusional interaction parameter, a high throughput tool to screen for high viscosity antibody solutions during lead candidate selection" Slides American Chemical Society National Meeting & Exposition, South San Francisco, CA USA, pp. 17 ( Mar. 28, 2011).
Corren et al., "Lebrikizumab treatment in adults with asthma" N Engl J Med 365(12):1088-1098 (Sep. 22, 2011).
Corry, D., "IL-13 in allergy: home at last" Current Opin Immunol 11:610-614 ( 1999).
Daugherty et al., "Formulation and delivery issues for monoclonal antibody therapeutics" Adv Drug Deliv Rev. 58:686-706 ( 2006).
DeSchryver-Kecskemeti et al., "Perineural and intraneural inflammatory infiltrates in the intestines of patients with systemic connective-tissue disease" Arch Pathol Lab Med 113(4):394-398 (Apr. 1989).
Development and optimization of protein formulation DS Application Not (www.microcalorimetry.com, pp. 5 ( Oct. 31, 2011).
Drug Delivery Systems Gerresheimer Catalog, Gerresheimer Bunde GmbH (16 pages), Apr. 2007.
Engineer et al., "Bullous pemphigoid: Interaction of interleukin 5, anti-basement membrane zone antibodies and eosinophils. A preliminary observation" Cytokine 13(1):32-38 (Jan. 7, 2001).
Falanga et al., "Frequency, levels, and significance of blood eosinophilia in systemic sclerosis, localized scleroderma, and eosinophilic fasciitis" J Am Acad Dermatol 17(4):648-656 ( 1987).
Feltelius et al., "Raised circulating levels of the eosinophil cationic protein in ankylosing spondylitis: relation with the inflammatory activity and the influence of sulphasalazine treatment" Ann Rheum Dis 46:403-407 ( 1987).
Garidel et al., "A thermodynamic analysis of the binding interaction between polysorbate 20 and 80 with human serum albumins and immunoglobulins: A contribution to understand colloidal protein stabilisation" Biophys Chem 143:70-78 ( 2009).
Goldberg et al., "Formulation development of therapeutic monoclonal antibodies using high-throughput fluorescence and static light scattering techniques: role of conformational and colloidal stability" J Pharm Sci 100(4):1306-1315 (Apr. 2011).
Gonlugur et al., "Non-allergic eosinophilic inflammation" Immunol Invest 35:29-45 (2006).
He et al., "High throughput Thermostability Screening of Monoclonal antibody formulations" J Pharm Sci 99(4):1707-1720 (Apr. 2010).
Hernnas et al., "Eosinophil cationic protein alters proteoglycan metabolism in human lung fibroblast cultures" Eur J Cell Biol 59(2):352-363 (Dec. 1992).
International Search Report and Written Opinion for International Patent Application No. PCT/US2005/044922 (2006).
International Search Report and Written Opinion for International Patent Application No. PCT/US2010/026410, 2010.
International Search Report and Written Opinion for Patent Application No. PCT/US2005/037471, (2007).
International Search Report and Written Report for International Patent Application No. PCT/US2012/62572, (2014).
Jezek et al., "Viscosity of concentrated therapeutic protein compositions" Advanced Drug Delivery Reviews 63:1107-1117 ( 2011).
Kashi, R.S., Challenges in the development of stable protein formulation, AAPS Symposium, Baltimore, MD (Sep. 9, 2011).
Kayser et al., "Glycosylation influences on the aggregation propensity of therapeutic monoclonal antibodies" Biotech J 6(1):38-44 ( 2011).
Kiang, P., "Future materials for prefilled syringe components" Am Pharm Rev:54-58 (Jul. 2, 2011).
Kivitz et al., "Clinical assessment of pain, tolerability, and preference of an autoinjection pen versus a prefilled syringe for patient self-administration of the fully human, monoclonal antibody adalimumab. The TOUCH trial", Clin Ther., 28(10):1619-1629 (2006).
Kolhe et al., "Impact of freezing on pH of buffered solutions and consequences for monoclonal antibody aggregation", Chemical Engineers Biotechnol, 26:727-733 (2010).
Krupsky et al., "Wegener's granulomatosis with peripheral eosinophilia Atypical variant of a classic disease" Chest 104(4):1290-1292 (Oct. 1993).
Kudlacz et al., "Functional effects of eotaxin are selectively upregulated on IL-5 transgenic mouse eosinophils" Inflammation 26(3):111-119 (Jun. 2002).
Lakhanpal et al., "Eosinophilic fasciitis: Clinical spectrum and therapeutic response in 52 cases" Semin Arthritis Rheum 17(4):221-231 (May 1988).
Le Brun et al., "A critical evaluation of self-interaction chromatography as a predictive tool for the assessment of protein-protein interactions in protein formulation development: a case study of a therapeutic monoclonal antibody" Eur J Pharm Biopharm 75:16-25 ( 2010).
Li et al., "Refractory periorbital edema in a 29-year-old man" Ann Allergy 69(2):101-105 (Aug. 1992).
Manning et al., "Stability of Protein Pharmaceuticals: An Update" Pharm Res 27(4):544-575 (Apr. 2010).
Mason et al., "Opalescence of an IgG2 monoclonal antibody solution as it relates to liquid-liquid phase separation" J. Pharmaceutical Sci 100(11):4587-4596 (Nov. 2011).
Mattern et al., "Formulation of proteins in vacuum-dried glasses. II. Process and storage stability in sugar-free amino acid Systems" Pharm Dev Technol 4(2):199-208 ( 1999).
Minton, A., "Static light scattering from concentrated protein solutions, I: General theory for protein mixtures and application to self-associating proteins" Biophysical J 93:1321-1328 (Aug. 2007).
Minton, A., "The effective hard particle model provides a simple, robust, and broadly applicable description of nonideal behavior in concentrated solutions of bovine serum albumin and other nonassociating proteins" J Pharm Sci 96(12):3466-3469 (Dec. 2007).
Miossec, P., "Cytokines and the pathophysiology of bone erosions in rheumatoid arthritis" J Clin Rheumatol 3( Suppl 2):S81-S83 (1997).

(56) References Cited

OTHER PUBLICATIONS

Neergaard et al., "Stability of monoclonal antibodies at high-concentration: head-to-head comparison of the IgG1 and IgG4 subclass" J Pharm Sciences 103(1):115-127 ( 2014).
Nielsen et al., "Assessment of IgE allergen specificity among latex-allergic health care workers: review of IgE-binding components of various latex extracts" Ann Allergy Asthma Immunol 85:489-494 (Dec. 2000).
Nishi et al., "Fc domain mediated self-association of an IgG1 monoclonal antibody under a low ionic strength condition" J Biosci Bioeng 112(4):326-332 ( 2011).
Nishi et al., "Phase separation of an IgGI antibody solution under a low ionic strength condition" Pharm Res 27:1348-1360 ( 2010).
Patapoff et al., "Polysorbate 20 prevents the precipitation of a monoclonal antibody during shear" Pharm Dev Technol 14(6):659-664 ( 2009).
Raghu et al., "An official ATS/ERS/JRS/ALAT statement: Idiopathic pulmonary fibrosis: Evidence-based guidelines for diagnosis and management" Am J Respir Crit Care Med 183:788-824 ( 2011).
Raghu et al., "Incidence and prevalence of idiopathic pulmonary fibrosis" Am J Respir Crit Care Med 174:810-816 ( 2006).
Richeldi et al., "Efficacy of a tyrosine kinase inhibitor in idiopathic pulmonary fibrosis" New Engl J Med 365(12):1079-1087 (Sep. 22, 2011).
Rzany et al., "Histopathological and epidemiological characteristics of patients with erythema exudativum multiforme major, Stevens-Johnson syndrome and toxic epidermal necrolysis" Br J Dermatol 135:6-11 ( 1996).
Saito et al., "Behavior of monoclonal antibodies: relation between the second virial coefficient (B 2) at low concentrations and aggregation propensity and viscosity at high concentrations" Pharm Res 29:397-410 ( 2012).
Salinas et al., "Understanding and modulating opalescence and viscosity in a monoclonal antibody formulation" J Pharm Sci 99(1):82-93 ( 2010).
Saluja et al., "Application of high-frequency rheology measurements for analyzing protein-protein interactions in high protein concentration solutions using a model monoclonal antibody (IgG2)" J Pharm Sci 95(9):1967-1983 (Sep. 2006).
Scherer et al., "Intermolecular interactions of IgG1 monoclonal antibodies at high concentrations characterized by light scattering" J Phys Chem B 114:12948-12957 ( 2010).
Scherer et al., "Issues and challenges of subvisible and submicron particulate analysis in protein solutions" AAPS J 14(2):236-243 (Jun. 2012).
Scherer, T., "Combination of product development for high concentration MAb therapeutics" Slides 3rd Annual Prefilled Syringe Conference, California, USA, pp. 22 ( May 16, 2012).
Scherer, T., "Implications of molecular interactions of MAbs at high concentrations & mitigation strategies" Slides 8th Annual Protein Engineering Summit (CHI-PEGS 2012), South San Francisco, CA USA, pp. 21 ( May 3, 2012).
Scherer, T., "Implications of molecular interactions of MAbs at high concentrations" Slides IBC Formulation Strategies for Protein Therapeutics, South San Francisco, CA USA, pp. 32 ( Nov. 1, 2011).
Sukhorukov et al., Punkcia i caterizacia ven, St. Petersburg Medical Publishing, pp. 3-4 (2001) in English translation.
Sukumar et al., "Opalescent appearance of an IgG1 antibody at high concentrations and its relationship to noncovalent association" Pharm Res 21(7):1087-1098 (Jul. 2004).
Supplementary European Search Report for European Patent Application No. EP 12 84 6324 dated Aug. 5, 2015.
Thabut et al., "Survival after bilateral versus single-lung transplantation for idiopathic pulmonary fibrosis" Annals of Internal Medicine 151:767-774 ( 2009).
Tian et al., "Calorimetric investigation of protein/amino acid interactions in the solid state" Int J Pharm 310:175-186 ( 2006).
Tian et al., "Spectroscopic evaluation of the stabilization of humanized monoclonal antibodies in amino acid formulations" Int J Pharm 335:20-31 ( 2007).
Vancheri et al., "Human Lung Fibroblast-derived granulocyte-macrophage colony stimulating factor (GM-CSF) mediates eosinophil survival in vitro" Am J Respir Cell Mol Biol 1:289-295 ( 1989).
Varga et al., "Eosinophilia-myalgia syndrome, eosinophilic fasciitis, and related fibrosing disorders" Curr Opin Rheumatol 9(6):562-570 ( 1997).
Volkin et al. Development and Manufacture of Protein Pharmaceuticals "Preformulation studies as an essential guide to formulation development and manufacture of protein pharmaceuticals" Nail and Akers, New York:Kluwer Academic/Plenum Publishers, vol. 14:1-46 ( 2002).
Wang et al., "Instability, stabilization, and formulation of liquid protein pharmaceuticals" Int J Pharm 185(2):129-188 (1999).
Webb, S., "Attacks on asthma" Nat Biotechnol 29(10):860-863 ( 2011).
Xia et al., "Light scattering by bovine a-crystallin proteins in solution: hydrodynamic structure and interparticle interaction" Biophys J 66:861-872 (Mar. 1994).
Xia et al., "Structural basis of eye lens transparency: light scattering by concentrated solutions of bovine α-crystallin proteins" Biophys J 71:2815-2822 (Nov. 1996).
Yadav et al., "Establishing a link between amino acid sequences and self-associating and viscoelastic behavior of two closely related monoclonal antibodies" Pharm ES 28:1750-1764 ( 2011).
Yadav et al., "Factors affecting the viscosity in high concentration solutions of different monoclonal antibodies" J Pharm Sci 99(12):4812-4829 (Dec. 2010).
Yadav et al., "Specific interactions in high concentration antibody solutions resulting in high viscosity" J Pharm Sci 99(3):1152-1168 (Mar. 2010).
Yadav et al., "Viscosity analysis of high concentration bovine serum albumin aqueous solutions" Pharm Res 28:1973-1983 ( 2011).
Yadav et al., "Viscosity behavior of high-concentration monoclonal antibody solutions: correlation with interaction parameter and electroviscous effects" J Pharm Sci 101(3):998-1011 (Mar. 2012).
Yetiser et al., "Eosinophilic granuloma of the bilateral temporal bone" Int J Pediatr Otorhinolaryngol 62:169-173 (2002).
Zheng et al., "The impact of glycosylation on monoclonal antibody conformation and stability" mAbs 3(6):568-576 ( 2011).
Zhou et al., "Biologics formulation factors affecting metal leachables from stainless steel", AAPS PharmSciTech, 12(1):411-421 (2011).

\* cited by examiner

ANTIBODY FORMULATIONS

CROSS REFERENCE TO RELATED APPLICATIONS

This application is a divisional of U.S. patent application Ser. No. 14/259,882, filed Apr. 23, 2014, issued as U.S. Pat. No. 10,000,562, which is a continuation of International Application No. PCT/US2012/062572 having an international filing date of Oct. 30, 2012, which claims the benefit of priority of provisional U.S. Application No. 61/553,916 filed Oct. 31, 2011, each of which are hereby incorporated by reference in their entirety.

FIELD

Formulations comprising an anti-IL-13 antibody are provided, including pharmaceutical formulations and methods of using such, formulations.

SEQUENCE LISTING

The instant application contains a Sequence Listing which has been submitted in ASCII format via EFS-Web and is hereby incorporated by reference in its entirety. Said ASCII copy, created on Jun. 7, 2018, is named 12279-792-999 SEQ LISTING.txt and is 22,879 bytes in size.

BACKGROUND

The interleukin (IL)-13 is a pleiotropic T helper cell subclass 2 (Th2) cytokine. It has been postulated that IL13 may play a more significant role than other Th2 cytokines In effector functions associated with the symptoms of asthma (Corry, Curr. Opin. Immunol., 11: 610 (1999)), Humanized anti-IL-13 antibodies have been described. See, e.g., Intn'l Pub. No. 2005/062967. One particular anti-IL13 antibody, lebrildzumab, has been clinically investigated for the treatment of patients with poorly controlled asthma. Certain of those results have been described in Corren et al., N Engl J Med 365(12): 1088-98 (2011), Because proteins, including antibodies, are larger and more complex than traditional organic and inorganic drugs (e.g., possessing multiple functional groups in addition to complex three-dimensional structures), the formulation of such proteins poses special problems. For a protein to remain biologically active, a formulation must preserve intact the conformational integrity of at least a core sequence of the protein's amino acids while at the same time protecting the protein's multiple functional groups from degradation. Degradation pathways for proteins can involve chemical instability (e.g., any process which involves modification of the protein by bond formation or cleavage resulting in a new chemical entity) or physical instability (e.g., changes in the higher order structure of the protein). Chemical instability can result from deamination, racemization, hydrolysis, oxidation, beta elimination or disulfide exchange. Physical instability can result from denaturation, aggregation, precipitation or adsorption, for example. The three most common protein degradation pathways are protein aggregation, deamination and oxidation, Cleland et al Critical Reviews in Therapeutic Drug Carrier Systems 10(4): 307-377 (1993).

High concentration (e.g., >100 mg/mL) liquid antibody formulations are desirable, for example, for routes of therapeutic administration or for therapeutic applications where small volumes of drug product are advisable, for example, for subcutaneous injection. High concentration antibody formulations, however, pose numerous challenges and problems. One problem, is instability due to the formation of particulates. With reconstituted liquid formulations, this problem has been addressed through the use of surfactants (e.g., a polysorbate), but surfactants are sometimes thought unsuitable for liquid formulations, because they render further processing difficult. Moreover, surfactants further do not reduce the increased viscosity caused as a result of numerous intermolecular interactions from the macromolecular nature of antibodies.

Although surfactants have been shown to significantly reduce the degree of particulate, formation of proteins, they do not address the problem of increased viscosity that makes difficult the manipulation and administration of concentrated antibody formulations. Antibodies tend to form, viscous solutions at high concentration because of their macromolecular nature and potential for intermolecular interactions. Moreover, pharmaceutically acceptable sugars are often used as stabilizers. Such sugars can enhance the intermolecular interactions, thereby increasing the viscosity of the formulation. Highly viscous formulations are difficult to manufacture, draw into a syringe and inject subcutaneously. The use of force in manipulating the viscous formulations leads to excessive frothing, which can lead to denaturation and inactivation of active biologies.

Certain formulations for high concentration antibodies have been described. See, e.g., Intn'n Pub. Nos. 2006/065746 and 2002/30463. Those publications do not specifically describe high concentration anti-IL13 antibodies.

It would be highly advantageous to have formulations comprising an anti-IL-13 antibody having extended stability and low viscosity at high antibody concentrations. High antibody concentration, formulations having such properties would be highly advantageous for certain routes of administration, e.g., for subcutaneous administration. The formulations provided herein address these needs and provide other useful benefits.

All references cited herein, including patent applications and publications, are incorporated by reference in their entirety for any purpose.

SUMMARY

The compositions of the invention are based, at least in part, on the discovery that anti-IL13 antibody described herein, lebrikizumab, can be formulated at high concentration (>100 mg/mL) in a histidine buffer containing polyol and surfactant and that such high antibody concentration formulation is of low viscosity, has extended physical and chemical stability and maintains potency. Compositions or formulations of the invention are useful for, e.g., the treatment of asthma and other lung disorders such as idiopathic pulmonary fibrosis and certain allergic, autoimmune and other inflammatory disorders. In addition, such formulation can be packaged into subcutaneous administration devices as described herein with maintenance of, for example, product stability and other desirable attributes.

Accordingly, in one aspect, a formulation comprising an anti-IL13 antibody is provided. In certain embodiments, the concentration of antibody in the formulation is at least 100 mg/mL and the viscosity of the formulation is less than 15 centipoise (cP) at 25° C. In another embodiment, the anti-IL13 antibody comprises three heavy chain CDRs, CDR-H1 having the amino acid sequence of SEQ ID NO.: 1, CDR-H2 having the amino acid sequence of SEQ ID NO.: 2, and CDR-H3 having the amino acid sequence of SEQ ID NO.: 3, and three light chain CDRs, CDR-L1 having the amino acid sequence of SEQ ID NO.: 4, CDR-L2 having the amino acid sequence of SEQ ID NO.: 5, and CDR-L3 having the amino acid sequence of SEQ ID NO.: 6. In one embodiment, the anti-IL13 antibody comprises a heavy chain variable region having the amino acid sequence of SEQ ID NO.: 7. In one embodiment, the anti-IL13 antibody comprises a light chain variable region having the amino acid sequence of SEQ ID NO.: 9. In one embodiment, the anti-IL13 antibody comprises a heavy chain having the amino acid sequence of SEQ ID NO.: 10. In one embodiment, the anti-IL13 antibody comprises a light chain having the amino acid sequence of SEQ ID NO.: 14. In one embodiment, the anti-IL13 antibody comprises a heavy chain variable region having the amino acid sequence of SEQ ID NO.: 7 and a light-chain variable region having the amino acid sequence of SEQ ID NO.: 9. In one embodiment, the anti-IL13 antibody comprises a heavy chain having the amino acid sequence of SEQ ID NO.: 10 and a light chain having the amino acid sequence of SEQ ID NO.: 14. In one embodiment, the concentration of antibody is 125 mg/mL. In one embodiment, the concentration of antibody is 150 mg/mL.

In another aspect, the formulation comprises histidine acetate buffer, ph 5.4 to 6.0, and the histidine acetate concentration in the buffer is between 5 mM and 40 mM. In certain embodiments, the formulation comprises a polyol and a surfactant and the concentration of the polyol in the formulation is between 100 mM and 200 mM and the concentration of the surfactant in the formulation is between 0.01% and 0.1%. In certain embodiments, the polyol is sucrose and the surfactant is polysorbate 20. In certain embodiments, the histidine acetate buffer is pH 5.7 and the histidine acetate concentration in the buffer is 20 mM, and the concentration of sucrose in the formulation is 175 mM and the concentration of polysorbate 20 is 0.03%. In one embodiment, the concentration of antibody is 125 mg/mL or 150 mg/mL. In one embodiment, the anti-IL-13 antibody comprises three heavy chain CDRs, CDR-H1 having the amino acid sequence of SEQ ID NO.: 1, CDR-H2 having the amino acid sequence of SEQ ID NO.: 2, and CDR-H3 having the amino acid sequence of SEQ ID NO.: 3, and three light chain CDRs, CDR-L1 having the amino acid sequence of SEQ ID NO.: 4, CDR-L2 having the amino acid sequence of SEQ ID NO.: 5, and CDR-L3 having the amino acid sequence of SEQ ID NO.: 6.

In yet another aspect, the formulation comprises an anti-IL13 antibody in a histidine acetate buffer, pH 5.4 to 6.0, and the histidine acetate concentration in the buffer is between 5 mM and 40 mM and the concentration of antibody in the formulation is at least 100 mg/mL. In certain embodiments, the formulation further comprises a polyol and a surfactant, and the concentration of the polyol in the formulation is between 100 mM and 200 mM and the concentration of the surfactant in the formulation is between 0.01% and 0.1%. In one embodiment, the polyol is sucrose and the surfactant is polysorbate 20. In one embodiment, the histidine acetate buffer is pH 5.7 and the histidine acetate concentration in the buffer is 20 mM, and wherein the concentration of sucrose in the formulation is 175 mM and the concentration of polysorbate 20 is 0.03%. In one embodiment, the anti-IL13 antibody comprises three heavy chain CDRs, CDR-H1 having the amino acid sequence of SEQ ID NO.: 1, CDR-H2 having the amino acid sequence of SEQ ID NO.: 2, and CDR-H3 having the amino acid sequence of SEQ ID NO.: 3, and three light chain CDRs, CDR-L1 having the amino acid sequence of SEQ ID NO.: 4, CDR-L2 having the amino acid sequence of SEQ ID NO.: 5, and CDR-L3 having the amino acid sequence of SEQ ID NO.: 6. In one embodiment, the anti-IL13 antibody comprises a heavy chain variable region having the amino acid sequence of SEQ ID NO.: 7. In one embodiment, the anti-IL13 antibody comprises a light chain variable region having the amino acid sequence of SEQ ID NO.: 9. In one embodiment, the anti-IL13 antibody comprises a heavy chain having the amino acid sequence of SEQ ID NO.: 10. In one embodiment, the anti-IL13 antibody comprises a light chain having the amino acid sequence of SEQ ID NO.: 14. In one embodiment, the anti-IL13 antibody comprises a heavy chain variable region having the amino acid sequence of SEQ ID NO.: 7 and a light chain variable region having the amino acid sequence of SEQ ID NO.: 9. In one embodiment, the anti-IL13 antibody comprises a heavy chain having the amino acid sequence of SEQ ID NO.: 10 and a light chain having the amino acid sequence of SEQ ID NO.: 14. In one embodiment, the formulation has a viscosity of less than 15 centipoise (cP) at 25° C. In one embodiment, the concentration of antibody is 125 mg/mL. In one embodiment, the concentration of antibody is 150 mg/mL.

In still another aspect, a formulation comprising an antiIL-13 antibody having extended stability is provided. In certain embodiments, the antibody concentration is at least 100 mg/mL and the viscosity is less than 15 centipoise (cP) at 25° C. In one embodiment, the antiIL-13 antibody is stable for at least one year at 5° C. In one embodiment, the antiIL-13 antibody is stable for at least two years at 5° C. In one embodiment, the anti-IL13 antibody is stable for three years at 5° C. In one embodiment, the anti-IL13 antibody is stable for at least four weeks at 25° C., or at least 8 weeks at 25° C., or at least 12 weeks at 25° C., or for 26 weeks at 4° C. In one embodiment, the formulation comprises histidine acetate buffer, ph 5.4 to 6.0, and the histidine acetate concentration in the buffer is between 5 mM and 40 mM. In one embodiment, the formulation further comprises a polyol and a surfactant, and the concentration of the polyol in the formulation is between 100 mM and 200 mM and the concentration of the surfactant in the formulation is between 0.01% and 0.1%. In one embodiment, the polyol is sucrose and the surfactant is polysorbate 20. In one embodiment, the histidine acetate buffer is pH 5.7 and the histidine acetate concentration in the buffer is 20 mM, and the concentration of sucrose in the formulation is 175 mM and the concentration of polysorbate 20 is 0.03%. In one embodiment, the concentration of antibody is 125 mg/mL or 150 mg/mL. In one embodiment, the anti-IL13 antibody comprises three heavy chain CDRs, CDR-H1 having the amino acid sequence of SEQ ID NO.: 1, CDR-H2 having the amino acid sequence of SEQ ID NO.: 2, and CDR-H3 having the amino acid sequence of SEQ ID NO.: 3, and three light chain CDRs, CDR-L1 having the amino acid sequence of SEQ ID NO.: 4, CDR-L2 having the amino acid sequence of SEQ ID NO.: 5, and CDR-L3 having the amino acid sequence of SEQ ID NO.: 6.

In yet another aspect, a formulation comprising an anti-IL13 antibody having extended stability in 20 mM histidine acetate buffer, pH 5.7, 175 mM sucrose, 0.03% polysorbate 20 is provided. In one embodiment, the concentration of antibody in the formulation is 125 mg/mL and the viscosity of the formulation is less than 15 centipoise (cP) at 25° C. In one embodiment, the concentration of antibody in the formulation is 150 mg/mL and the viscosity of the formulation is less than 15 centipoise (cP) at 25° C. In one embodiment, the anti-IL13 antibody comprises three heavy chain CDRs, CDR-H1 having the amino acid sequence of SEQ ID NO.: 1, CDR-H2 having the amino acid sequence of SEQ ID NO.: 2, and CDR-H3 having the amino acid sequence of SEQ ID NO.: 3, and three light chain CDRs, CDR-L1 having the amino acid sequence of SEQ ID NO.: 4, CDR-L2 having the amino acid sequence of SEQ ID NO.: 5, and CDR-L3 having the amino acid sequence of SEQ ID NO.: 6. In one embodiment, the anti-IL13 antibody comprises a heavy chain variable region having the amino acid sequence of SEQ ID NO.: 7 and a light chain variable region having the amino acid sequence of SEQ ID NO.: 9. In one embodiment, the anti-IL13 antibody comprises a heavy chain having the amino acid sequence of SEQ ID NO.: 10 and a light chain having the amino acid sequence of SEQ ID NO.: 14.

In still a further aspect, an article of manufacture comprising a subcutaneous administration device is provided. In certain embodiments, the subcutaneous administration device delivers to a patient a flat dose of an anti-IL13 antibody. In one embodiment, the flat dose is 37.5 mg of anti-IL13 antibody. In one embodiment, the flat dose is 75 mg of anti-IL13 antibody. In one embodiment, the flat dose is 125 mg of anti-IL13 antibody. In one embodiment the flat dose is 150 mg of anti-IL13 antibody. In certain embodiments, the anti-IL13 antibody is lebrikizumab. The anti-IL 13 antibody in the subcutaneous administration device is formulated in a buffer and other excipients as described above such that it is provided in a stable pharmaceutical formulation. In certain embodiments, the subcutaneous administration device is a prefilled syringe comprising a glass barrel, a plunger rod comprising a plunger stopper and a needle. In certain embodiments, the subcutaneous administration device further comprises a needle shield and optionally a needle shield device. In certain embodiments, the volume of formulation contained in the prefilled syringe is 0.3 mL, 1 mL, 1.5 mL, or 2.0 mL, in certain embodiments, the needle is a staked-in needle comprising a 3-bevel tip or a 5-bevel tip. In certain embodiments, the needle is between 25 gauge (G) and 30 G and is between ½ inch, long and ⅝ inch long. In one embodiment, the subcutaneous administration device comprises a prefilled 1.0 mL low tungsten borosilicate glass (type I) syringe and a stainless steel 5-bevel 27 G ½ inch long thin-wall staked-in needle. In certain embodiments, the subcutaneous administration device comprises a rigid needle shield. In certain embodiments, the rigid needle shield comprises a rubber formulation having low zinc content. In one embodiment, the needle shield is rigid and comprises an elastomeric component, FM27/0, and rigid polypropylene shield. In certain embodiments, the plunger rod comprises a rubber plunger stopper. In certain embodiments, the rubber plunger stopper comprises 4023/50 rubber and FluroTec® ethylene-tetrafluoroethylene (ETFE) coating. In certain embodiments, the subcutaneous administration device comprises a needle safety device. Exemplary needle safety devices include, but are not limited to, Ultrasafe Passive® Needle Guard X100L (Safety Syringes, Inc.) and Rexam Safe n Sound™ (Rexam).

In yet another aspect, a method of treating asthma in a patient is provided. In certain embodiments, the method comprises administering to the patient an effective amount of any of the above formulations. In certain embodiments, the effective amount is 0.3 mL, one-half mL, one mL or two mL, or about 0.3 mL, about one-half mL, about one mL or about two mL. In another aspect, a method of treating idiopathic pulmonary fibrosis in a patient is provided. In certain embodiments, the method comprises administering to the patient an effective amount of any of the above formulations. In certain embodiments, the effective amount is one-half mL, one mL or two mL, or about one-half mL, about one mL or about two mL.

In still yet another aspect, methods of administering subcutaneously a formulation comprising and anti-IL13 antibody are provided. Such methods comprise administering subcutaneously any of the anti-IL13 antibody formulations described above. In certain embodiments, the methods comprise a subcutaneous administration device according to any of the devices described above.

DETAILED DESCRIPTION

Figure 1:
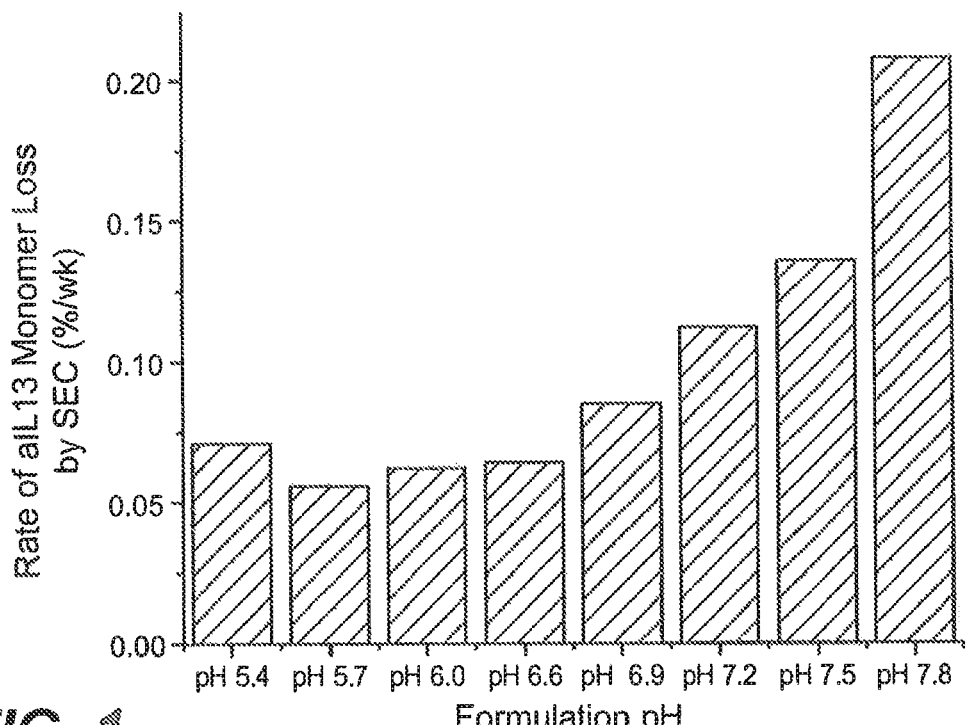
FIG. 1 shows the rate of anti-IL13 antibody monomer degradation per week as a function of pH as described in Example 1.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

Certain Definitions

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

As used in this specification and the appended claims, the singular forms "a," "an" and "the" include plural referents unless the context clearly dictates otherwise. Thus, for example, reference to "a protein" or an "antibody" includes a plurality of proteins or antibodies, respectively; reference to "a cell" includes mixtures of cells, and the like.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

A "sterile" formulation is aseptic or free or essentially free from all living microorganisms and their spores.

A "frozen" formulation is one at a temperature below 0° C. Generally, the frozen formulation is not freeze-dried, nor is it subjected to prior, or subsequent, lyophilization. In certain embodiments, the frozen formulation comprises frozen drug substance for storage (in stainless steel tank) or frozen drag product (in final vial configuration).

A "stable" formulation is one in which the protein therein essentially retains its physical stability and/or chemical stability and/or biological activity upon storage. In certain embodiments, the formulation essentially retains its physical and chemical stability, as well as its biological activity upon storage. The storage period is generally selected based on the intended shelf-life of the formulation.

As used herein, a formulation having "extended stability" means one in which the protein therein essentially retains its physical stability, chemical stability, and biological activity upon storage at 5° C. for one year or more. In certain embodiments, the storage is at 5° C. for two years or more. In certain embodiments, the storage is at 5° C. for up to three years.

A protein "retains its physical stability" in a pharmaceutical formulation if it shows no signs or very little of aggregation, precipitation and/or denaturation upon visual examination of color and/or clarity, or as measured by UV light scattering or by size exclusion chromatography.

A protein "retains its chemical stability" in a pharmaceutical formulation, if the chemical stability at a given time is such that the protein is considered to still retain its biological activity as defined below. Chemical stability can be assessed by detecting and quantifying chemically altered forms of the protein. Chemical alteration may involve size modification (e.g. clipping) which can be evaluated using size exclusion chromatography, SDS-PAGE and/or matrix-assisted laser desorption ionization/time-of-flight mass spectrometry (MALDI/TQF MS), for example. Other types of chemical alteration include charge alteration (e.g. occurring as a result of deamidation) which can be evaluated by ion-exchange chromatography or imaged capillary isoelectric focusing (icIEF), for example.

An antibody "retains its biological activity" in a pharmaceutical formulation, if the biological activity of the antibody at a given time is within about 10% (within the errors of the assay) of the biological activity exhibited at the time the pharmaceutical formulation was prepared as determined in an antigen binding assay or a potency assay, for example.

Herein, "biological activity" of a monoclonal antibody refers to the ability of the antibody to bind to antigen. It can further include antibody binding to antigen and resulting in a measurable biological response which can be measured in vitro or in vivo. Such activity may be antagonistic or agonistic.

A "deamidated" monoclonal antibody is one in which one or more asparagine residues thereof has been derivitized, e.g. to an aspartic acid or an iso-aspartic acid.

An antibody which is "susceptible to deamidation" is one comprising one or more residues which has been found to be prone to deamidate.

An antibody which is "susceptible to aggregation" is one which has been found to aggregate with other antibody molecule(s), especially upon freezing and/or agitation.

An antibody which is "susceptible to fragmentation" is one which has been found to be cleaved into two or more fragments, for example at a hinge region thereof.

By "reducing deamidation, aggregation, or fragmentation" is intended preventing or decreasing the amount of deamidation, aggregation, or fragmentation relative to the monoclonal antibody formulated at a different pH or in a different buffer.

The antibody which is formulated is essentially pure and desirably essentially homogeneous (e.g., Tree from contaminating proteins etc). "Essentially pure" antibody means a composition comprising at least about 90% by weight of the antibody, based on total weight of the composition, or at least about 95% by weight. "Essentially homogeneous"

antibody means a composition comprising at least about 99% by weight of antibody, based on total weight of the composition.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

As used herein, "buffer" refers to a buffered solution that resists changes in pH by the action of its acid-base conjugate components.

A "histidine buffer" is a buffer comprising histidine ions. Examples of histidine buffers include histidine chloride, histidine acetate, histidine phosphate, histidine sulfate, histidine succinate, etc. In one embodiment, the histidine buffer is histidine acetate. In one embodiment, the histidine acetate buffer is prepared by titrating L-histidine (free base, solid) with acetic acid (liquid). In certain embodiments, the histidine buffer or histidine-acetate buffer is between pH 4.5 to 6.5. In certain embodiments, the histidine buffer or histidine-acetate buffer is between pH 5.4 to 6.0. In one embodiment, the buffer has a pH of 5.6. In one embodiment, the buffer has a pH of 5.7. In one embodiment, the buffer has a pH of 5.8.

Herein, a "surfactant" refers to a surface-active agent, typically a nonionic surfactant. Examples of surfactants herein include polysorbate (for example, polysorbate 20 and, polysorbate 80); poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropy-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUA™ series (Mona Industries, Inc., Paterson, N.J.); polyethyl glycol, polypropyl glycol, and copolymers of ethylene and propylene glycol (e.g. Pluronics, PF68 etc); etc. In one embodiment, the surfactant is polysorbate 20.

A "preservative" is a compound which can be optionally included in the formulation to essentially reduce bacterial action therein, thus facilitating the production of a multi-use formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. In one embodiment, the preservative herein is benzyl alcohol.

A "polyol" is a substance with multiple hydroxyl groups, and includes sugars (reducing and nonreducing sugars), sugar alcohols and sugar acids. A polyol may optionally be included in the formulation. In certain embodiments, polyols herein have a molecular weight which is less than about 600 kD (e.g. in the range from about 120 to about 400 kD). A "reducing sugar" is one which contains a hemiacetal group that can reduce metal ions or react covalently with lysine and other amino groups in proteins and a "nonreducing sugar" is one which does not have these properties of a reducing sugar. Examples of reducing sugars are fructose, mannose, maltose, lactose, arabinose, xylose, ribose, rhamnose, galactose and glucose. Nonreducing sugars include sucrose, trehalose, sorbose, melezitose and raffinose. Mannitol, xylitol, erythritol, threitol, sorbitol and glycerol are examples of sugar alcohols. As to sugar acids, these include L-gluconate and metallic salts thereof. Where it is desired that the formulation is freeze-thaw stable, the polyol is typically one which does not crystallize at freezing temperatures (e.g. −200 C) such that it destabilizes the antibody in the formulation. In one embodiment, the polyol is a nonreducing sugar. In one such embodiment, the nonreducing sugar is sucrose.

As used herein, "asthma" refers to a complex disorder characterized by variable and recurring symptoms, reversible airflow obstruction (e.g., by bronchodilator) and bronchial hyperresponsiveness which may or may not be associated with underlying inflammation. Examples of asthma include aspirin sensitive/exacerbated asthma, atopic asthma, severe asthma, mild asthma, moderate to severe asthma, corticosteroid naïve asthma, chronic asthma, corticosteroid resistant asthma, corticosteroid refractory asthma, newly diagnosed and untreated asthma, asthma due to smoking, asthma uncontrolled on corticosteroids and other asthmas as mentioned in J Allergy Clin Immunol (2010) 126(5):926-938.

As used herein, "treatment" refers to clinical intervention in an attempt to alter the natural course of the individual or cell being treated, and can be performed before or during the course of clinical pathology. Desirable effects of treatment include preventing the occurrence or recurrence of a disease or a condition or symptom thereof, alleviating a condition or symptom of the disease, diminishing any direct or indirect pathological consequences of the disease, decreasing the rate of disease progression, ameliorating or palliating the disease state, and achieving remission or improved prognosis.

An "effective amount" refers to an amount effective, at dosages and for periods of time necessary, to achieve the desired therapeutic or prophylactic result. A "therapeutically effective amount" of a therapeutic agent may vary according to factors such as the disease state, age, sex, and weight of the individual, and the ability of the antibody to elicit a desired response in the individual. A therapeutically effective amount is also one in which any toxic or detrimental effects of the therapeutic agent are outweighed by the therapeutically beneficial effects.

An "individual," "subject" or "patient" is a vertebrate. In certain embodiments, the vertebrate is a mammal. Mammals include, but are not limited to, primates (including human and non-human primates) and rodents (e.g., mice and rats). In certain embodiments, a mammal is a human.

A "medicament" is an active drug to treat a disease, disorder, and/or condition.

"Antibodies" (Abs) and "immunoglobulins" (Igs) refer to glycoproteins having similar structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact, monoclonal antibodies), polyclonal antibodies, monovalent antibodies, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

The terms "full length antibody," "intact antibody" and "whole antibody" are used herein interchangeably to refer to an antibody in its substantially intact form, not antibody fragments as defined below. The terms particularly refer to an antibody with heavy chains that contain the Fc region.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is a minimum antibody fragment which contains a complete antigen-binding site. In one embodiment, a two-chain Fv species consists of a dimer of one heavy- and one light-chain variable domain in tight, non-covalent association. Collectively, the six CDRs of an Fv confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group, F(ab')$_2$ antibody fragments originally were produced as pairs of Fab' fragments which have hinge cysteines between them. Other chemical couplings of antibody fragments are also known.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., *Nature,* 256: 495 (1975); Harlow et al., *Antibodies: A Laboratory Manual*, (Cold Spring Harbor Laboratory Press, 2$^{nd}$ ed, 1988); Hammerling et al, in: *Monoclonal Antibodies and T-Cell Hybridomas* 563-681 (Elsevier, N.Y., 1981)), recombinant DNA methods (see, e.g., U.S. Pat. No. 4,816,567), phage display technologies (see, e.g., Clackson et al., *Nature,* 352: 624-628 (1991); Marks et al., *J. Mol Biol* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al, *Proc. Natl. Acad. Sci. USA* 90: 2551 (1993): Jakobovits et al., *Nature* 362: 255-258 (1993); Bruggemann et al., *Year in Immunol* 7: 33 (1993); U.S. Pat. Nos. 5,545, 807; 5,545,806; 5,569,825; 5,625,126; 5,633,425; 5,661, 016; Marks et al., *Bio. Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol* 14: 826 (1996) and Lonberg and Huszar, *Intern. Rev. Immunol* 13: 65-93 (1995).

The monoclonal antibodies herein specifically include "chimeric" antibodies in which a portion of the heavy and/or light chain is identical wish or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81: 6855-9855 (1984)).

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150: 880-887 (1993); Clarkson et al., Nature 352: 624-628 (1991).

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101(H3). (Chothia and Lesk, J. Mol. Biol. 196: 901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, Front, Biosci. 13: 1619-1633 (2008).) Unless otherwise indicated, HVR residues and other residues in the variable domain (e.g., FR residues) are numbered herein according to Kabat et al., supra.

A "human antibody" is one which comprises an amino acid sequence corresponding to that of an antibody produced by a human and/or has been made using any of the techniques for making human antibodies as disclosed herein. Such techniques include screening human-derived combinatorial libraries, such as phage display libraries (see, e.g., Marks et al, J. Mol. Biol., 222: 581-597 (1991) and Hoogenboom et al., Nucl. Acids Res., 19: 4133-4137 (1991)); using human myeloma and mouse-human heteromyeloma cell lines for the production of human monoclonal antibodies (see, e.g., Kozbor J. Immunol., 133: 3001 (1984); Brodeur et al, Monoclonal Antibody Production Techniques and Applications, pp. 55-93 (Marcel Dekker, Inc., New York, 1987); and Boerner et al, J. Immunol 147: 86 (1991)); and generating monoclonal antibodies in transgenic animals (e.g., mice) that are capable of producing a full repertoire of human antibodies in the absence of endogenous immunoglobulin production (see, e.g., Jakobovits et al, Proc. Natl. Acad. Sci USA, 90: 2551 (1993); Jakobovits et al, Nature, 362: 255 (1993); Bruggermann et al, Year in Immunol., 7: 33 (1993)). This definition of a human antibody specifically excludes a humanized antibody comprising antigen-binding residues from a non-human animal.

An "affinity matured" antibody is one with one or more alterations in one or more CDRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. Bio/Technology 10: 779-783 (1992) describes affinity maturation by VH and VL domain shuffling. Random mutagenesis of HVR and/or framework residues is described by: Barbas et al Proc Nat. Acad. Sci. USA 91: 3809-3813 (1994); Schier et al Gene 169: 147-155 (1995); Yelton et al J. Immunol 155: 1994-2004 (1995); Jackson et al, J. Immunol 154(7):3310-9 (1995); and Hawkins et al, J. Mol. Biol 226: 889-896 (1992).

A "blocking antibody" or an "antagonist antibody" is one which inhibits or reduces a biological activity of the antigen it binds. Certain blocking antibodies or antagonist antibodies partially or completely inhibit the biological activity of the antigen.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively.

As used herein, "anti-IL13 antibody," also referred to as lebrikizumab, means a humanized IgG4 antibody that binds human IL13. In one embodiment, the anti-IL13 antibody comprises three heavy chain CDRs, CDR-H1 (SEQ ID NO.: 1), CDR-H2 (SEQ ID NO.: 2), and CDR-H3 (SEQ ID NO.: 3). In one embodiment, the anti-IL13 antibody comprises three light chain CDRS, CDR-L1 (SEQ ID NO.: 4), CDR-L2 (SEQ ID NO.: 5), and CDR-L3 (SEQ ID NO.: 6). In one embodiment, the anti-L13 antibody comprises three heavy chain CDRs and three light chain CDRs, CDR-H1 (SEQ ID NO.: 1), CDR-H2 (SEQ ID NO.: 2), CDR-H3(SEQ ID NO.: 3), CDR-L1 (SEQ ID NO.: 4), CDR-L2 (SEQ ID NO.: 5), and CDR-L3 (SEQ ID NO.: 6), In one embodiment, the anti-IL13 antibody comprises a variable heavy chain region, VH, having an amino acid sequence selected from SEQ ID NOs. 7 and 8. In one embodiment, the anti-IL13 antibody comprises a variable light chain region, VL, having the amino acid sequence of SEQ ID NO.: 9. In one embodiment, the anti-IL13 antibody comprises a variable heavy chain region, VH, having an amino acid sequence selected from SEQ ID NOs. 7 and 8 and a variable light chain region, VL, having an amino acid sequence of SEQ ID NO.: 9. In one embodiment, the anti-IL13 antibody comprises a heavy chain having an amino acid sequence of SEQ ID NO.: 10 or SEQ ID NO.: 11 or SEQ ID NO.: 12 or SEQ ID NO.: 13. In one embodiment, the anti-IL13 antibody comprises a light chain having the amino acid sequence of SEQ ID NO.: 14. In one embodiment, the anti-IL13 antibody comprises a heavy chain having an amino acid sequence selected from SEQ ID NO.: 10, SEQ ID NO.: 11, SEQ ID NO.: 12, and SEQ ID NO.: 13 and a light chain having the amino acid sequence of SEQ ID NO.: 14. Anti-IL13 antibodies are further described in Intn'l Pub. No. 2005/062967.

An "isolated" biological molecule, such as a nucleic acid, polypeptide, or antibody, is one which has been identified and separated and/or recovered from at least one component of its natural environment.

Reference to "about" a value or parameter herein includes (and describes) embodiments that are directed to that value or parameter per se. For example, description referring to "about X" includes description of "X."

A "subcutaneous administration device" refers to a device which is adapted or designed to administer a drug, for example a therapeutic antibody, or pharmaceutical formulation by the subcutaneous route. Exemplary subcutaneous administration devices include, but are not limited to, a syringe, including a pre-filled syringe, an injection device, infusion pump, injector pen, needleless device, and patch delivery system. A subcutaneous administration device administers a certain volume of the pharmaceutical formulation, for example about 1.0 mL, about 1.25 mL, about 1.5 mL, about 1.75 mL, or about 2.0 mL.

A "package insert" or "label" is used to refer to instructions customarily included in commercial packages of therapeutic products or medicaments, that contain information about the indications, usage, dosage, administration, contraindications, other therapeutic products to be combined with the packaged product, and/or warnings concerning the use of such therapeutic products or medicaments and the like.

A "kit" is any manufacture (e.g., a package or container) comprising at least one reagent, e.g., a medicament for treatment of asthma or other lung disorder. In certain embodiments, the manufacture is promoted, distributed, or sold as a unit for performing the methods of the present invention.

A "target audience" is a group of people or an institution to whom or to which a particular medicament is being promoted or intended to be promoted, as by marketing or advertising, especially for particular uses, treatments, or indications, such as individual patients, patient populations, readers of newspapers, medical literature, and magazines, television or internet viewers, radio or internet listeners, physicians, drug companies, etc.

The term "serum sample" refers to any serum sample obtained from an individual. Methods for obtaining sera from mammals are well known in the art.

The term "whole blood" refers to any whole blood sample obtained from an individual. Typically, whole blood contains all of the blood components, e.g., cellular components and plasma. Methods for obtaining whole blood from mammals are well known in the art.

The "amount" or "level" of a biomarker associated with an increased clinical benefit to a patient suffering from a certain disease or disorder, or predictive of response to a particular therapeutic agent or treatment regimen, is a detectable level in a biological sample. These can be measured by methods known to one skilled in the art and also disclosed herein. The expression level or amount of biomarker assessed can be used to determine the response or the predicted response to a treatment or therapeutic agent.

The terms "level of expression" or "expression level" in general are used interchangeably and generally refer to the amount of an amino acid product or protein in a biological sample. "Expression" generally refers to the process by which gene-encoded information is converted into the structures present and operating in the cell. Therefore, as used herein, "expression" of a gene may refer to transcription into a polynucleotide, translation into a protein, or even post-translational modification of the protein.

Asthma and Other Lung Diseases and Certain Allergic, Autoimmune and Other Inflammatory Diseases Asthma is described as a chronic pulmonary disease that involves airway inflammation, hyperresponsiveness and obstruction. Physiologically, airway hyperresponsiveness is documented by decreased bronchial airflow after bronchoprovocation with methacholine or histamine. Other triggers that provoke airway obstruction include cold air, exercise, viral upper respiratory infection, cigarette smoke, and respiratory allergens. Bronchial provocation with allergen induces a prompt early phase immunoglobulin E (IgE)-mediated decrease in bronchial airflow followed in many patients by a late-phase IgE-mediated reaction with a decrease in bronchial airflow for 4-8 hours. The early response is caused by acute release of inflammatory substances, such as histamine, PGD¬2¬, leukotriene, tryptase and platelet activating factor (PAF), whereas the late response is caused by de novo synthesized pro-inflammatory cytokines (e.g. TNFα, IL4, IL13) and chemokines (e.g. MCP-1 and MIP-1α) (Busse et al In: Allergy: Principles and Practice, Ed. Middleston, 1173 (1998)). In chronic asthmatic patients, persistent pulmonary symptoms are mediated by the heightened response of Th2 cells. Th2 cytokines are believed to play a vital role in the disease (Larche et al., J. Allergy Clin. Immunol., 111: 450 (2003)), in particular, IL13 and IL4 produced by Th2 cells with NK phenotype (NKT) in the airway as indicated in a model of asthma in rodents (Akbari et al, Nature Med., 9: 582 (2003)). The gross pathology of asthmatic airways displays lung hyperinflation, smooth muscle hypertrophy, lamina reticularis thickening, mucosal edema, epithelial cell sloughing, cilia cell disruption, and mucus gland hypersecretion. Microscopically, asthma is characterized by the presence of increased numbers of eosinophils, neutrophils, lymphocytes, and plasma cells in the bronchial tissues, bronchial secretions, and mucus. Initially, there is recruitment of leukocytes from the bloodstream to the airway by activated CD4+ T-lymphocytes. The activated T-lymphocytes also direct the release of inflammatory mediators from eosinophils, mast cells, and lymphocytes. In addition, the Th2 cells produce IL4, IL5, IL9 and IL13, IL4, in conjunction with IL13, signals the switch from IgM to IgE antibodies.

Cross-linking of membrane-bound IgE molecules by allergen causes mast cells to degranulate, releasing histamine, leukotrienes, and other mediators that perpetuate the airway inflammation. IL5 activates the recruitment and activation of eosinophils. The activated mast cells and eosinophils also generate their cytokines that help to perpetuate the inflammation. These repeated cycles of inflammation in the lungs with injury to the pulmonary tissues followed by repair may produce long-term structural changes ("remodeling") of the airway Moderate asthma is currently treated with a daily inhaled anti-inflammatory-corticosteroid or mast cell inhibitor such as cromolyn sodium or nedocromil plus an inhaled beta2- agonist as needed (3-4 times per day) to relieve breakthrough symptoms or allergen- or exercise-induced asthma. Cromolyn sodium and nedocromil block bronehospasm and inflammation, but are usually effective only for asthma that is associated with allergens or exercise and typically, only for juvenile asthmatics. Inhaled corticosteroids improve inflammation, airways hyperreactivity, and obstruction, and reduce the number of acute exacerbations. However, it takes at least a month before effects are apparent and up to a year for marked improvement to occur. The most frequent side effects are hoarseness and oral fungal infection, i.e., candidiasis. More serious side effects have been reported, e.g., partial adrenal suppression, growth inhibition, and reduced bone formation, but only with the use of higher doses. Beclomethasone, triamcinolone, and flunisolide probably have a similar potency; whereas budesonide and fluticasone are more potent and reportedly have fewer systemic side effects.

Even patients with mild disease show airway inflammation, including infiltration of the mucosa and epithelium with activated T cells, mast cells, and eosinophils. T cells and mast cells release cytokines that promote eosinophil growth and maturation and the production of IgE antibodies, and these, in turn, increase microvascular permeability, disrupt the epithelium, and stimulate neural reflexes and mucus-secreting glands. The result is airways hyperreactivity, bronchoconstriction, and hypersecretion, manifested by wheezing, coughing, and dyspnea.

Traditionally, asthma has been treated with oral and inhaled bronchodilators. These agents help the symptoms of asthma, but do nothing for the underlying inflammation. Recognition during the last decade or of the importance of inflammation in the etiology of asthma has led to the increased use of corticosteroids, but many patients continue to suffer from uncontrolled asthma.

In addition to asthma, other diseases that may be treated by the formulations of the inventions include allergy, autoimmune disease, or other inflammatory diseases. Other allergic diseases include allergic rhinitis, atopic dermatitis, food hypersensitivity and urticaria; immune-mediated skin diseases include bullous skin diseases, erythema multiform and contact dermatitis; autoimmune disease include psoriasis, rheumatoid arthritis, juvenile chronic arthritis; inflammatory bowel disease (i.e., ulcerative colitis, Crohn's disease); other diseases associated with IL13 include idiopathic interstitial pneumonia, goblet cell metaplasia, inflammatory and fibrotic lung diseases such as cystic fibrosis, gluten-sensitive enteropathy, and Whipple's disease; immunologic diseases of the lung such as eosinophilic pneumonia, idiopathic pulmonary fibrosis and hypersensitivity pneumonitis; chronic obstructive pulmonary disease, RSV infection, uveitis, scleroderma, osteoporosis, and Hodgkin's lymphoma.

Idiopathic pulmonary fibrosis (IPF) is disorder amenable to treatment with the formulations of the invention. IPF is a restrictive lung disease characterized by progressive interstitial fibrosis of lung parenchyma, affecting approximately 100,000 patients in the United States (Raghu et al., *Am J Respir Crit Care Med* 174: 810-816 (2006)). This interstitial fibrosis associated with IPF leads to progressive loss of lung function, resulting in death due to respiratory failure in most patients. The median survival from the time of diagnosis is 2-3 years (Raghu et al., *Am J Respir Crit Care Med* 183: 788-824 (2011)). The etiology and key molecular and pathophysiological drivers of IPF are unknown. The only treatment shown to prolong survival in IPF patients is lung transplantation (Thabut et al., *Annals of internal medicine* 151: 767-774 (2009)). Lung transplantation, however, is associated with considerable morbidity, not all IPF patients are appropriate candidates for it, and there is a relative paucity of suitable donor lungs. Despite numerous attempts, no drug therapies to date have been shown to substantially prolong survival in a randomized, placebo-controlled interventional trial in IPF patients, although some interventions have appeared to slow the rate of lung function decline in some patients (Raghu et al., *Am J Respir Crit Care Med* 183: 788-824 (2011); Richeldi et al., *The New England J. of Med.* 365: 1079-1087 (2011)).

Although the prognosis for all IPF patients is dire, there is considerable heterogeneity in disease trajectory (Raghu et al., *Am J Respir Crit Care Med* 183: 788-824 (2011)). Some patients exhibit a relatively indolent course, losing lung function at a relatively constant rate over as long as 10 years or more, while others experience a more rapid decline in lung function, succumbing to death within a year or two of diagnosis. In addition, some patients suffer from acute exacerbations of the disease, typically characterized by sudden dramatic decreases in lung function. Generally, these patients do not fully recover after the acute event and often die during or shortly after an exacerbation. This heterogeneity in disease trajectory suggests that different IPF patients may have different pathophysiological factors underlying their disease, which may be differentially susceptible to molecularly targeted therapeutics such as formulations of the invention.

Eosinophilic inflammation is associated with a variety of illnesses, both allergic and non-allergic (Gonlugur (2006) Immunol. Invest. 35(1):29-45). Inflammation is a restorative response of living tissues to injury. A characteristic of inflammatory reactions is the accumulation of leukocytes in injured tissue due to certain chemicals produced in the tissue itself. Eosinophil leukocytes accumulate in a wide variety of conditions such as allergic disorders, helminthic infections, and neoplastic diseases (Kudlaez et al., (2002) Inflammation 26: 111-119). Eosinophil leukocytes, a component of the immune system, are defensive elements of mucosal surfaces. They respond not only to antigens but to parasites, chemicals, and trauma.

Tissue eosinophilia occurs in skin diseases such as eczema, pemphigus, acute urticaria, and toxic epidermal necrolysis as well as in atopic dermatitis ([Rzany et al., 1996]). Eosinophils accumulate in the tissue and empty granule proteins in IgE-mediated allergic skin reactions ([Nielsen et al., 2001]). Eosinophils combined with mast cells are likely to cause joint inflammation (Miossec et al., 1997). Eosinophilic inflammation sometimes accompanies joint trauma. Synovial fluid eosinophilia can be associated with diseases such as rheumatoid arthritis, parasitic disease, hypereosinophilic syndrome, Lyme disease, and allergic processes, as well as hemarthrosis and arthrography ([Atanes et al., 1996]). Eosinophilic inflammation can affect bones as well ([Yetiser et al., 2002]). Examples of eosinophilic muscle disease include eosinophilic perimyositis, eosinophilic polymyositis, and focal eosinophilic myositis ([Lakhanpal et al., 1988]). Eosinophilic inflammations affecting skeletal muscles may be associated with parasite infections or drugs or features of some systemic disorders of hypereosinophilia (e.g., idiopathic hypereosinophilic syndrome and eosinophilia-myalgia syndrome. Eosinophils participate in the inflammatory response to epitopes recognized by autoimmune antibodies ([Engineer et al., 2001]). Connective tissue diseases may lead to neutrophilic, eosinophilic, or lymphocytic vascular inflammations ([Chen et al., 1996]). Tissue and peripheral blood eosinophilia can occur in active rheumatismal diseases. Elevation of serum ECP levels in ankylosing spondylitis, a kind of connective tissue disease, suggests that eosinophils are also involved in the underlying process (Feltelius et al., 1987). Wegener's granulomatosis can rarely present with pulmonary nodules, pleural effusion, and peripheral blood eosinophilia ([Krupsky et al., 1993]).

Peripheral blood eosinophilia of at least 400/mm3 can occur in 7% of cases of systemic sclerosis, 31% of cases of localized scleroderma, and 61% of cases of eosinophilic fasciitis ([Falanga and Medsger, 1987]). Scleroderma yields an inflammatory process closely resembling Meissner's and Auerbach's plexuses and consists of mast cells and eosinophil leukocytes in the gastrointestinal system. Eosinophil-derived neurotoxins can contribute to gastrointestinal motor dysfunction, as occurs in scleroderma ([de Schryver Kecskemeti and Clouse, 1989]).

Eosinophils can accompany localized ([Varga and Kahari, 1997]) or systemic ([Bouros et al., 2002]) connective tissue proliferation. They can incite fibrosis by inhibiting proteoglycan degradation in fibroblasts ([Hernnas et al., 1992]), and fibroblasts mediate eosinophil survival by secreting GM-CSF ([Vancheri et al., 1989]), Eosinophils can be found in nasal ([Bacherct et al., 2001]), bronchial ([Arguelles and Blanco, 1983]), and gastrointestinal polyp tissues ([Assarian and Sundaresori, 1985]). Likewise, eosinophils can be localized in inflammatory pseudotumors (myofibroblastic tumor). Eosinophils often accompany inflammatory pseudotumors in the orbital region, in which case the condition can mimic angioedema or allergic rhinoconjunctivitis ([Li et al., 1992]).

Eosinophilic inflammation can be found in tissue trauma (e.g., as a result of surgery or injury). Eosinophilic inflammation can also be associated with cardiovascular illnesses (e.g., eosinophilic myocarditis, eosinophilic coronary arteritis, ischemic heart disease, acute myocardial infarction, cardiac rupture). Necrotic inflammatory processes can also involve eosinophilic inflammation (polymyositis, coronary artery dissection, necrotizing lesions of neuro-Behcet's disease, dementia, cerebral infarction).

Certain Therapeutic Agents

A therapeutic agent for the treatment of asthma and other lung diseases is provided herein. In one embodiment, therapeutic agent is an anti-IL13 antibody, also referred to as lebrikizumab. Lebrikizumab as an IgG4 antibody. In one embodiment, the anti-IL13 antibody comprises three heavy chain CDRs, CDR-H1 (SEQ ID NO.: 1), CDR-H2 (SEQ ID NO.: 2), and CDR-H3 (SEQ ID NO.: 3). In one embodiment, the anti-IL13 antibody comprises three light chain CDRs, CDR-L1 (SEQ ID NO.: 4), CDR-L2 (SEQ ID NO.: 5), and CDR-L3 (SEQ ID NO.: 6). In one embodiment, the anti-IL13 antibody comprises three heavy chain CDRs and three light chain CDRs, CDR-H1 (SEQ ID NO.: 1), CDR-H2 (SEQ ID NO.: 2), CDR-H3 (SEQ ID NO.: 3), CDR-L1 (SEQ ID NO.: 4), CDR-L2 (SEQ ID NO.: 5), and CDR-L3 (SEQ ID NO.: 6). In one embodiment, the anti-IL13 antibody comprises a variable heavy chain region, VH, having an amino acid sequence selected from SEQ ID NOs. 7 and 8. In one embodiment, the anti-11,13 antibody comprises a variable light chain region, VL, having the amino acid sequence of SEQ ID NO.: 9. In one embodiment, the anti-IL13 antibody comprises a variable heavy chain region, VH, having an amino acid sequence selected from SEQ ID NOs. 7 and 8 and a variable light chain region, VL, having an amino acid sequence of SEQ ID NO.: 9. In one embodiment, the anti-IL13 antibody comprises a heavy chain having the amino acid sequence of SEQ ID NO.: 10 or SEQ ID NO.: 11 or SEQ ID NO.: 12 or SEQ ID NO.: 13. In one embodiment, the anti-IL13 antibody comprises a light chain having the amino acid sequence of SEQ ID NO.: 14. In one embodiment, the anti-IL13 antibody comprises a heavy chain having an amino acid sequence selected from SEQ ID NO.: 10, SEQ ID NO.: 11, SEQ ID NO.: 12, and SEQ ID NO.: 13 and a light chain having the amino acid sequence of SEQ ID NO.: 14. Anti-IL13 antibodies are further described in Intn'l Pub. No. 2005/062967.

In another aspect, an anti-IL-13 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO.: 8. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-IL-13 antibody comprising that sequence retains the ability to bind to human EL-13. In certain embodiments, a total of 1 to 10 amino acids have been substituted, altered inserted and/or deleted in SEQ ID NO.: 8. In certain embodiments, substitutions, insertions, or deletions occur in regions outside the CDRs (i.e., in the FRs). Optionally, the anti-IL13 antibody comprises the VH sequence in SEQ ID NO.: 8, including post-translational modifications of that sequence.

In another aspect, an anti-IL-13 antibody is provided, wherein the antibody comprises a light chain variable domain (VL) having at least 90%, 91%, 92%, 93%, 94%, 95%, 96%, 97%, 98%, 99%, or 100% sequence identify to the amino acid sequence of SEQ ID NO.: 9. In certain embodiments, a VL sequence having at feast 90%, 91%, 92%, 93%, 94%, 95%, 96%, 97%, 98%, or 99% identity contains substitutions (e.g., conservative substitutions), insertions, or deletions relative to the reference sequence, but an anti-IL-13 antibody comprising that sequence retains the ability to bind to IL-13. In certain embodiments, a total of 1 to 10 amino acids have been substituted, inserted and/or deleted in SEQ ID NO.: 9. In certain embodiments, the substitutions, insertions, or deletions occur in regions outside the CDRs (i.e., in the FRs). Optionally, the anti-IL-13 antibody comprises the VL sequence in SEQ ID NO.: 9, including post-translational modifications of that sequence.

In yet another embodiment, the anti-IL-13 antibody comprises a VL region having at least 90%, 91%, 92%, 93%, 94%, 95%, 96%, 97%, 98%, 99%, or 100% sequence identity to the amino acid sequence of SEQ ID NO.: 9 and a VH region having at least 90%, 91%, 92%, 93%, 94%, 95%, 96%, 97%, 98%, 99%, or 100% sequence identity to the amino acid sequence of SEQ ID NO.: 8.

Certain Molecular Biomarkers

In certain instances, biomarkers, e.g., serum biomarkers, are quantitated in a biological sample obtained from a patient as a means of selecting patients for treatment with a given therapeutic agent. U.S. Application Nos. 61/459,760, 61/465,425, 61/484,650, and 61/574,485 ("Diagnosis and Treatments Related to TH2 Inhibition) describe a periostin assay and methods selecting patients for treatment with the anti-IL13 antibody formulations described herein.

General Techniques for Formulations

Formulations comprising anti-IL13 antibodies may be prepared and analyzed using certain excipients and techniques known in the art and as further described herein. In certain embodiments, the antibody to be formulated has not been subjected to prior lyophilization and the formulation of interest herein is an aqueous formulation. In certain embodiments, the antibody is a full length antibody. In one embodiment, the antibody in the formulation is an antibody fragment, such as an F(ab')2, in which case problems that may not occur for the full length antibody (such as clipping of the antibody to Fab) may need to be addressed. The therapeutically effective amount of antibody present in the formulation is determined by taking into account the desired dose volumes and mode(s) of administration, for example. From about 0.1 mg/mL to about 250 mg/mL, or from, about 10 mg/mL to about 200 mg/mL or from about 50 mg/mL to about 175 mg/ml, is an exemplary antibody concentration in the formulation. In one embodiment, the anti-IL13 antibody is formulated at a concentration of 125 mg/mL. In one embodiment, the anti-IL13 antibody is formulated at a concentration of 150 mg/mL.

An aqueous formulation is prepared comprising the antibody in a pH-buffered solution. In certain embodiments, the buffer of has a pH in the range from about 4.5 to about 6.5. In certain embodiments the pH is in the range from pH of 5.0 to 6.0, or in the range from pH 5.25 to 5.75, or in the range from pH 5.3 to 5.6. In certain embodiments of the invention, the formulation has a pH of 5.6 or about 5.6. In certain embodiments of the invention, the formulation has a pH of 5.7 or about 5.7. In certain embodiments of the invention, the formulation has a pH of 5.8 or about 5.8. Examples of buffers that will control the pH within this range include acetate (e.g. histidine acetate, arginine acetate, sodium acetate), succinate (such as histidine succinate, arginine succinate, sodium succinate), gluconate, citrate and other organic acid buffers and combinations thereof. The buffer concentration can be from about 1 mM to about 600 mM, depending, for example, on the buffer and the desired isotonicity of the formulation. In certain embodiments, the contain histidine in the concentration from about 5 mM to 40 mM. In one embodiment, the buffer is 20 mM histidine acetate, pH 5.7. In certain embodiments, the buffer is 20 mM histidine succinate, pH 5.7.

A surfactant can optionally be added to the antibody formulation. Exemplary surfactants include nonionic surfactants such as polysorbates (e.g. polysorbates 20, 80 etc) or poloxamers (e.g. poloxamer 188). The amount of surfactant added is such that it reduces aggregation of the formulated antibody and/or minimizes the formation of particulates in the formulation and/or reduces adsorption. For example, the surfactant may be present in the formulation in an amount from about 0.001% to about 0.5%, or from about 0.005% to about 0.2%, or from, about 0.01% to about 0.1%. In one embodiment, the surfactant is polysorbate 20 present in the formulation in an amount of 0.03%.

In one embodiment, the formulation contains the above-identified agents (e.g., antibody, buffer, and surfactant) and is essentially free of one or more preservatives, such as benzyl alcohol, phenol, m-cresol, chlorobutanol and benzethonium Cl. In one embodiment, the formulation does not comprise a preservative. In another embodiment, a preservative may be included in the formulation, particularly where the formulation is a multidose formulation. The concentration of preservative may be in the range from about 0.1% to about 2%, or from about 0.5% to about 1%. One or more other pharmaceutically acceptable carriers, excipients or stabilizers such as those described in Remington's Pharmaceutical Sciences 16th edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; anti-oxidants including ascorbic acid and methionine; chelating agents such as EDTA; metal complexes (e.g. Zn-protein complexes); biodegradable polymers such as polyesters; and/or salt-forming counterions.

While the various descriptions of chelators herein often focus on EDTA, it will be appreciated that other metal ion chelators are also encompassed within the invention. Metal ion chelators are well known by those of skill in the art and include, but are not necessarily limited to aminopolycarboxylates, EDTA (ethylenediaminetetraacetic acid), EGTA (ethylene glycol-bis(beta-aminoethyl ether)-N,N,N',N'-tetraacetic acid), NTA (nitrilotriacetic acid), EDDS (ethylene diamine disuccinate), PDTA (1,3-propylenediaminetetraacetic acid), DTPA (diethylenetriaminetetraacetic acid), ADA (beta-alaninediacetic acid), MGCA (methylglycinediacetic acid), etc. Additionally, some embodiments herein comprise phosphonates/phosphonic acid chelators. In certain embodiments, the formulation contains methionine.

Tonicity agents, sometimes known as "stabilizers" are present to adjust or maintain the tonicity of a liquid composition. When used with large, charged biomolecules such as proteins and antibodies, they are often termed "stabilizers" because the can interact with the charged groups of the amino acid side chains, thereby lessening the potential for inter and intra-molecular interactions. Tonicity agents can be present in any amount between 0.1% to 25% by weight, or 1 to 5%, taking into account the relative amounts of the other ingredients. Tonicity agents include polyhydric sugar alcohols, thrihydric or higher sugar alcohols, such as glycerin, erythritol, arabitol, xylitol, sorbitol and mannitol.

Additional stabilizers include a broad range of excipients which range in function from bulking agents to solubility enhancers, to agents preventing denaturation or adherence to the container wall. Stabilizers can be present in the range from 0.1 to 10,000 parts per weight active protein or antibody. Typical stabilizers include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinositol, galactose, galacfifol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), Pluronic® polyols, Triton®, polyoxyethylene sorbitan monoethers (Tween®-20, Tween®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

Various analytical techniques for measuring protein stability are available in the art and are reviewed in Peptide and Protein Drug Delivery, 247-301, Vincent Lee Ed., Marcel Dekker, Inc., New York, N.Y., Pubs, (1991) and Jones, A. Adv. Drug Delivery Rev. 10: 29-90 (1993), for example. Stability can be measured at a selected temperature for a selected time period. In certain embodiments, the formulation is stable at about 40° C. for at least about 2-4 weeks, and/or stable at about 5° C. for at least 3 months, and/or stable at about 5° C. for at least six months, and/or stable at about 5° C. for at least 12 months and/or stable at about −20° C. for at least 3 months or at least I year. In certain embodiments, the formulation is stable at about 25° C. for least 6 months and/or stable at about 25° C. for 12 months, and/or stable at about 5° C. for 6 months, and/or stable at about 5° C. for 12 months, and/or stable at about −20° C. for at least 6 months, and/or stable at about −20° C. for at least 12 months, and/or stable at 5° C. or −20° C. for at least two years. In certain embodiments, the formulation is stable following freezing (to, e.g., −70° C.) and thawing of the formulation, for example following 1, 2 or 3 cycles of freezing and thawing. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography, image capillary isoelectric focusing (icIEF) or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g. Asn deamidation), oxidation (e.g. Met oxidation), isomerization (e.g. Asp isomerization), clipping/hydrolysis/fragmentation (e.g. hinge region fragmentation), succinimide formation, impaired cysteine(s), N-terminal extension, C-terminal processing, glycosylation differences, etc.

The formulations to be used for in vivo administration should be sterile. This is readily accomplished by filtration through sterile filtration membranes, prior to, or following, preparation of the formulation.

A therapeutic agent can be administered in accordance with known methods, such as intravenous administration as a bolus or by continuous infusion over a period of time, by intramuscular, intraperitoneal, intracerobrospinal, subcutaneous, infra-articular, intrasynovial, intrathecal, oral, topical, or inhalation routes. Optionally, administration may be performed through mini-pump infusion using various commercially available devices.

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition, supra.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. Microencapsulation of recombinant proteins for sustained release has been successfully performed with human growth hormone (rhGH), interferon-(rhIFN−), interleukin-2, and MN rpg 120. Johnson et al., Nat. Med. 2: 795-799 (1996); Yasuda et al., Biomed. Ther. 27: 1221-1223 (1993); Hora et al., Bio/Technology 8: 755-758 (1990); Cleland, "Design and Production of Single Immunization Vaccines Using Polylactide Polyglycolide Microsphere Systems," in Vaccine Design: The Subunit and Adjuvant Approach, Powell and Newman, eds., (Plenum Press: New York, 1995), pp. 439-462; WO 97/03692; WO 96/40072; WO 96/07399; and U.S. Pat. No. 5,654,010.

The sustained-release formulations of these proteins may be developed using poly lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer", in Biodegradable Polymers as Drag Delivery Systems (Marcel Dekker; New York, 1990), M. Chasin and R. Langer (Eds.) pp. 1-14.

While polymers such as ethylene-vinyl acetate and lactic acid-glycolic acid enable release of molecules for over 100 days, certain hydro gels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecutar S—S bond formation through thio-disulfide interchange, stabilization may be achieved by modifying sulfhydryl residues, lyophilizing from acidic solutions, controlling moisture content, using appropriate additives, and developing specific polymer matrix compositions.

Liposomal or proteinoid compositions may also be used to formulate the proteins or antibodies disclosed herein. See U.S. Pat. Nos. 4,925,673 and 5,013,556.

Stability of the proteins and antibodies described herein may be enhanced through the use of non-toxic "water-soluble poly valent metal salts". Examples include $Ca^{2+}$, $Mg^{2+}$, $Zn^{2+}$, $Fe^{2+}$, $Fe^{3+}$, $Cu^{2+}$, $Sn^{2+}$, $Sn^{4+}$, $Al^{2+}$ and $Al^{3+}$. Example anions that can form water soluble salts with the above polyvalent metal cations include those formed from inorganic acids and/or organic acids. Such water-soluble salts have a solubility in water (at 20° C.) of at least about 20 mg/ml, alternatively at least about 100 mg/ml, alternative at least about 200 mg/ml.

Suitable inorganic acids that can be used to form the "water soluble polyvalent metal salts" include hydrochloric, acetic, sulfuric, nitric, thiocyanic and phosphoric acid. Suitable organic acids that can be used include aliphatic carboxylic acid and aromatic acids. Aliphatic acids within this definition may be defined as saturated or unsaturated C2-9 carboxylic acids (e.g., aliphatic mono-, di- and tri-carboxylic acids). For example, exemplary monocarboxylic acids within this definition include the saturated C2-9 monocarboxylic acids acetic, proprionic, butyric, valeric, caproic, enanthic, caprylic pelargonic and capryonic, and the unsaturated C2-9 monocarboxylic acids acrylic, propriolic methacrylic, crotonic and isocrotonic acids. Exemplary dicarboxylic acids include the saturated C2-9 dicarboxylic acids malonic, succinic, glutaric, adipic and pimelic, while unsaturated C2-9 dicarboxylic acids include maleic, fumaric, citraconic and mesaconic acids. Exemplary tricarboxylic acids include the saturated C2-9 tricarboxylic acids tricarballylic and 1,2,3-butanetricarboxylic acid. Additionally, the carboxylic acids of this definition may also contain one or two hydroxyl groups to form hydroxy carboxylic acids. Exemplary hydroxy carboxylic acids include glycolic, lactic, glyceric, tartronic, malic, tartaric and citric acid. Aromatic acids within this definition include benzoic and salicylic acid.

Commonly employed water soluble polyvalent metal salts which may be used to help stabilize the encapsulated polypeptides of this invention include, for example: (1) the inorganic acid metal salts of halides (e.g., zinc chloride, calcium chloride), sulfates, nitrates, phosphates and thiocyanates; (2) the aliphatic carboxylic acid metal salts (e.g., calcium acetate, zinc acetate, calcium proprionate, zinc glycolate, calcium lactate, zinc lactate and zinc tartrate); and (3) the aromatic carboxylic acid metal salts of benzoates (e.g., zinc benzoate) and salicylates.

In certain embodiments, an anti-IL13 antibody is administered using, for example, a self-inject device, autoinjector device, or other device designed for self-administration. In certain embodiments, an anti-IL13 antibody is administered using a subcutaneous administration device. Various self-inject devices and subcutaneous administration devices, including autoinjector devices, are known in the art and are commercially available. Exemplary devices include, but are not limited to, prefilled syringes (such as BD HYPAK SCF®, READYFILL™, and STERIFILL SCF™ from Becton Dickinson; CLEARSHOT™ copolymer prefilled syringes from Baxter; and Daikyo Seiko CRYSTAL ZENITH® prefilled syringes available from West Pharmaceutical Services); disposable pen injection devices such as BD Pen from Becton Dickinson; ultra-sharp and microneedle devices (such as INJECT-EASE™ and microinfuser devices from Becton Dickinson; and H-PATCH™ available from Valeritas) as well as needle-free injection devices (such as BIOJECTOR® and IJECT® available from Bioject; and SOF-SERTER® and patch devices available from Medtronic). Certain embodiments of subcutaneous administration devices are described further herein. Co-formulations or co-administrations with such self-inject devices or subcutaneous administration devices of an anti-IL13 antibody with at least a second therapeutic compound are envisioned.

Recombinant Methods

Antibodies may be produced using recombinant methods and compositions, e.g., as described in U.S. Pat. No. 4,816,567. In one embodiment, isolated nucleic acid encoding an anti-IL13 antibody described herein is provided. Such nucleic acid may encode an amino acid, sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-IL13 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-IL13 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eucaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods In Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eucaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22: 1409-1414 (2004), and Li et al., Nat. Biotech. 24: 210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36: 59 (1977)); baby hamster kidney cells (BHK); mouse sertoli cells (TM4 cells as described, e.g., in Mather, Biol. Reprod. 23: 243-251 (1980)); monkey kidney cells (CV1); African green monkey kidney cells (VERO-76); human cervical carcinoma cells (HELA); canine kidney cells (MDCK; buffalo rat liver cells (RRL 3A); human lung cells (W138); human liver cells (Hep G2); mouse mammary tumor (MMT 060562); TRI cells, as described, e.g., in Mather et al., Annals N.Y. Acad. Sci, 383: 44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77: 4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

Assays

Anti-IL13 antibodies provided herein may be identified, screened for, or characterized for their physical/chemical properties and/or biological activities by various assays known in the art.

Binding Assays and Other Assays

In one aspect, an anti-IL13 antibody is tested for its antigen binding activity, e.g., by known methods such as ELISA, Western blot, etc.

In another aspect, competition assays may be used to identify an antibody that competes with anti-IL13 antibody for binding to IL13. In certain embodiments, such a competing antibody binds to the same epitope (e.g., a linear or a conformational epitope) that is bound by lebrikizumab or another anti-IL13 antibody specified herein. Detailed exemplary methods for mapping an epitope to which an antibody binds are provided in Morris (1996) "Epitope Mapping Protocols," in Methods in Molecular Biology vol. 66 (Humana Press, Totowa, N.J.).

In an exemplary competition assay, immobilized IL13 is incubated in a solution comprising a first labeled antibody that binds to IL13 (e.g., lebrikizumab) and a second unlabeled antibody that is being tested for its ability to compete with the first antibody for binding to IL13. The second antibody may be present in a hybridoma supernatant. As a control, immobilized IL13 is incubated in a solution comprising the first labeled antibody but not the second unlabeled antibody. After incubation under conditions permissive for binding of the first antibody to IL13, excess unbound antibody is removed, and the amount of label associated with immobilized IL13 is measured. If the amount of label associated with immobilized IL13 is substantially reduced in the test sample relative to the control sample, then that indicates that the second antibody is competing with the first antibody for binding to IL13. See Harlow and Lane (1988) Antibodies: A Laboratory Manual ch. 14 (Cold Spring Harbor Laboratory, Cold Spring Harbor, N.Y.).

Activity Assays

In one aspect, assays are provided for identifying anti-IL-13 antibodies having biological activity. Biological activity may include, e.g., activity in asthma. Antibodies having such biological activity in vivo and/or in vitro are also provided. In certain embodiments, an antibody of the invention is tested for such biological activity.

Articles of Manufacture and Kits

An article of manufacture is provided which contains the formulation and provides instructions for its use. The article of manufacture comprises a container. Suitable containers include, for example, bottles, vials (e.g. dual chamber vials), syringes (such as single or dual chamber syringes) and test tubes. The container may be formed from a variety of materials such as glass or plastic. The container holds the formulation and the label on, or associated with, the container may indicate directions for reconstitution and/or use. The label may further indicate that the formulation is useful or intended for subcutaneous administration. The container holding the formulation may be a multi-use vial, which allows for repeat administrations (e.g. from 2-6 administrations) of the reconstituted formulation. The article of manufacture may further comprise a second container comprising a suitable diluent (e.g. BWFI). Upon mixing of the diluent and the lyophilized formulation, the final protein concentration in the reconstituted formulation will generally be at least 50 mg/ml. The article of manufacture may further include other materials desirable from a commercial and user standpoint, including other buffers, diluents, filters, needles, syringes, and package inserts with instructions for use.

In certain embodiments, an article of manufacture comprising a subcutaneous administration device is provided which delivers to a patient a flat dose of an anti-IL13 antibody, wherein the flat dose is for example, but not limited to, 37.5 mg, 75 mg, or 125 mg, or 150 mg. In certain embodiments, the anti-IL13 antibody is lebrikizumab. The anti-IL13 antibody in the subcutaneous administration device is formulated in a buffer, for example, histidine pH 5.7, and other excipients, for example, sucrose and polysorbate, such that it is provided in a stable pharmaceutical formulation. In certain embodiments, the subcutaneous administration device is a prefilled syringe comprising a glass barrel with needle and optionally, a needle shield and also optionally, a needle shield device. In certain embodiments, the volume contained in the syringe is 0.5 mL, 1 mL, 1.5 mL, or 2.0 mL or about 0.5 mL, about 1 mL, about 1.5 mL, or about 2.0 mL. In certain embodiments, the needle is a staked-in needle comprising a 3-bevel tip or a 5-bevel tip. In certain embodiments, the needle is between 25 gauge (G) and 30 G. In certain embodiments, the needle is between ½ inch long and ⅝ inch long. In one embodiment, the subcutaneous administration device comprises a prefilled 1.0 mL low tungsten borosilicate glass (type I) syringe and a stainless steel 5-bevel 27 G ½ inch long thin-wall staked-in needle. In certain embodiments, the subcutaneous administration device comprises a rigid needle shield. In certain embodiments, the rigid needle shield comprises a rubber formulation having low zinc content, for example, FM27/0 (Dactwyler) and comprises a rigid polypropylene shield. In certain embodiments, the plunger rod comprises a rubber plunger stopper. In certain embodiments, the rubber plunger stopper comprises 4023/50 rubber and FluroTec® ethylene-tetrafluoroethylene (ETFE) coating (West Pharmaceutical Services, Inc.). In certain embodiments, the subcutaneous administration device comprises a needle safety device. Exemplary needle safety devices include, but are not limited to, Ultrasafe Passive® Needle Guard X100L (Safety Syringes, Inc.) and Rexam Safe n Sound™ (Rexam).

Additional devices suitable for subcutaneous delivery include for example, but not limited to, an injection device such as MJECT-EASE™ and GENJECT™ devices; an infusion pump such as ACCU-CHECK™; an injector pen such as GENPEN™; a needleless device such as MEDDCTOR™ and BIOJECTOR™; an autoinjector and a subcutaneous patch delivery system.

Kits will typically comprise the container described above and one or more other containers comprising materials desirable from a commercial and user standpoint, including buffers, diluents, filters, needles, syringes, and package inserts with instructions for use. A label may be present on the container to indicate that the composition is used for a specific therapy.

EXAMPLES

The following are examples of the formulations and methods of the invention. It is understood that various other embodiments may be practiced, given the general description provided above.

Example 1

Materials and Methods
Material and Sample Preparation Procedures

Except for anti-IL13, which is a humanized IgG4 monoclonal antibody, all other antibodies used in the experiments described below were humanized IgG1 monoclonal antibodies. Monoclonal antibodies were expressed in Chinese hamster ovarian (CHO) cell lines, and purified by a series of standard chromatography steps, including protein A and ion exchange chromatography methods. The purified antibodies were obtained as concentrated solutions from tangential flow filtration with added solution buffers and stabilizers. These were the stock antibody solutions used as starting materials for the studies described below.

These stock mAb starting materials were stored at 2-8° C. until further use. Additional preparation of mAb solutions included dialysis against low ionic strength buffer and filtration through 0.22 μm modified PVDF (polyvinylidene fluoride) filters (Millipore Steriflip, Millipore Corp., Mass.) to remove large particulates. Typically, mAb concentrations of 140-150 mg/mL after dialysis were obtained. To obtain higher mAb concentrations, 10 mL of mAb was concentrated with Amicon YM30 Centriprep (Millipore Corp, Mass.) concentrators centrifuged at 2700 rpm. Final mAb concentrations in the dialyzed and centrifugally concentrated preparations were determined by using gravimetric dilutions and absorptivities at 280 nm (A280) and measurement of UV absorption at 280 nm using an Agilent diode array Spectrophotometer model 8453 with a 1 cm path length quartz cuvette. Extinction coefficients were determined by quantitative amino acid analysis.

Monoclonal antibody solutions for light scattering experiments were prepared in 20 mL scintillation vials over 0.5-275 mg/mL by gravimetric dilution of known stock solution concentrations in a laminar flow hood. All scintillation vials were carefully cleaned with deionized water and dried in a stream of filtered compressed nitrogen gas. Before addition to protein solutions, all buffer and reagent solutions were additionally filtered through 0.10 um Whatman Anotop 25 filters. After preparation or dilution of the samples, mAb solutions were mixed to homogeneity and allowed to reach thermal and chemical equilibrium at controlled room temperature for 2 hours. Protein solutions were centrifuged at room temperature for 20-30 minutes at 3000 rpm to remove adventitious dust and bubbles from the solutions prior to use for light scattering. The higher concentration solutions (mAb>170 mg/mL) were centrifuged for greater lengths of time until the light scattering signal showed a minimum of noise. Exterior surfaces of scintillation vials were lightly coated with silicone oil to reduce undesired scattering from vial surface defects. Samples prepared as above were directly placed in the light scattering instrument for measurements.

Determination of $B_2$ by Multi-Angle Light Scattering

Sample preparation for light scattering utilized 20 mL Teflon®-lined septum cap vials which were cleaned with MilliQ water and dried under a stream of filtered nitrogen gas. Sample of various concentrations were prepared by taking an appropriate volume of the stock mAb solution at approximately 80 mg/mL, diluting first to approximately 8 mg/mL with the appropriate buffer, and then performing a final dilution with 20 mL of 0.2 μm filtered buffer. A total of eight protein concentrations (0.05-1.1 mg/mL mAb) for each buffer condition were equilibrated for 14-18 hours at room temperature prior to initiating measurements. All measurements were made as a series of solutions of increasing protein concentrations, with each experiment performed in triplicate. An Agilent solvent degasser and isocratic pump (Agilent, Palo Alto, Calif.), with a 25 mm Millipore (Millipore, Billerica, Mass.) solvent filter (PVDF, 0.1 μm), were used with a continuous flow rate of 0.5 mL/min. Sample injection was automated with a Gibson GX281 (Gilson, Inc., Middleton Wis.) liquid handling unit configured with a 2 mL injection loop and a Wyatt Technology Deutschland inline micro-filter with 0.1 μm, 10 mM PVDF membrane. Concentration and light scattering measurements were conducted in series, with an Agilent MWD UV detector measuring at 280 nm, followed by the 18-angle EOS MALS detector (Wyatt Technology Corporation, Santa Barbara, Calif.) with gain reduced to 21×. Data were acquired and processed in Astra™ 4.90.07 (WTC) software, with further analysis conducted by exporting slice results. Plots of $K*c/R(\theta=0)/K*c/$ or $1/M_{Wapp}$ vs. concentration with linear regression fitting of data give slope=$2B_2$, and an intercept of $1/M_{w0}$, the weight average molecular weight at infinite dilution.

High Concentration Multi-Angle Static Light Scattering (SLS)

An 18-angle Dawn EOS light scattering detector with a 30 mW solid state laser ($\lambda$=690 nm) from Wyatt Technology (Santa Barbara, Calif.) was used for all static light scattering measurements with a water-cooled Peltier temperature controller set at 23° C. The instrument was calibrated with 99.9% Toluene (Chromatography grade). For a typical scintillation vial experiment, a detector gain setting of 1× was used for all photodiodes, at fixed angles of 38° to 148°. Since the radius of gyration (Rg) of anti-CD11a is less than 10 nm, a dilute solution (1-2 mg/mL) of anti-CD11a was used at each salt concentration to normalize the angular dependency of the photodiodes relative to the 90° detector using a photodiode detector gain setting of 21× at the end of each experiment. Measurement of static light scattering intensity was conducted as a function of mAb concentration from 0.5 mg/mL to 275 mg/mL, and as a function of NaCl concentration (0-600 mM). Scattering data for each sample/vial was collected over an interval of 5-10 minutes with a data collection frequency of 12 points/minute. Astra 4.90.07 Software (Wyatt Technology Corporation, Santa Barbara, Calif.) was used to acquire and process the static Light scattering data, with a dn/dc value of 0.185 applied to calculations which could be exported as slice results. Further analysis and calculations with the exported results were conducted in Microsoft Excel, Origin v7.5, and MATLAB R14. For high concentration light scattering data, it was often easier to interpret the results in the format of $M_{Wapp}$ vs. mAb concentration, where increases in molecular weight corresponded to the presence of concentration dependent reversible self-association. (See, e.g., Scherer, T. M., et al. *The Journal of Physical Chemistry B* 114(40): 12948-12957 (2010); Mintom. A. P., *J Pharm Sci* 96(12): 3466-9 (2007); Minton, A. P. *Biophysical Journal* 93(4): 1321-1328 (2007).

Turbidity by UV Spectroscopy

The turbidities for tested protein solutions from the high concentration light scattering experiments and for protein solutions from the pH Screen experiment (each, as further described below) were measured at ambient temperature by using an Agilent 8453 Spectrophotometer. The turbidity was calculated as the average of the absorbance at wavelength 350 nm where the sum of the absorbance values over the wavelength range 340 rim to 360 nm at 5 nm increments was divided by 5. The measurements of protein solutions were performed in a small volume quartz cuvette with a 1 cm pathlength. Absorbance at 690 nm was also recorded.

Capillary Differential Scanning Calorimetry (DSC) Characterization of Melting Temperature (Tm)

Protein thermal conformational stability was assessed by using a MicroCal Capillary Differential Scanning Calorimeter. MAbs were diluted to 1 mg/mL in buffer. Five hundred microliters of the protein and its matching buffer were loaded into a 96 well, plate. The heat capacity was monitored as the temperature was increased from 15 to 95° C. at a scan rate of 60° C./hr. VPViewer 2000 Cap DSC was used to acquire the data and MicroCal, LLC DSC Data Analysis was used to analyze data. See Yadav, S. et al., *J Pharm Sci.* 99(3): 1152-68 (2010).

Nephelometry

Nephelometric measurements were made using a HACH (Model 2100AN IS) Laboratory Turbidimeter Instrument with 90 degree detection of scattered intensity. The detector was calibrated with Formazin standard 4000 nephelometric turbidity unit (NTU) stock solution, with 0-0.5 relative turbidity standard concentration. Samples were placed in cuvettes and measured in duplicate reporting mean NTH of the sample.

Rheology

Viscosities of samples were measured with a MCR300 rheometer (Anton Paar, Ashland, Va.) using a cone and plate measuring system. Samples were loaded onto the lower measuring plate and were allowed to come to thermal equilibrium at 25° C. A solvent trap was used to prevent solvent evaporation. The sample went through two cycles of shear-rate sweeps (each cycle includes ramping up from 10 $sec^{-1}$ to 1000 $sec^{-1}$, holding at 1000 $sec^{-1}$ for 1 minute, ramping down from 1000 $sec^{-1}$ to 10 $sec^{-1}$). There is one 1-minute resting time between the cycles. The reported value is the average of the two shear rate sweeps of one sample at 1000 $sec^{-1}$. The error bar represents the standard deviation of the two runs in units of milliPascal-second (mPas). The sample was under shear stress for 2 minutes total at 1000 $sec^{-1}$. We chose 1000 $sec^{-1}$ because the viscosity is relatively independent, of shear rates in this range (200 $sec^{-1}$<shear rate<2000 $sec^{-1}$). The viscosity difference between two aliquots of one sample was within ±0.5 mPa at 1000 $sec^{-1}$. The duration of measurement at each shear rate was optimized using US200 software (Anton Paar, Ashland, Va.).

Cloud Temperature Determination

For a system that undergoes liquid-liquid phase separation (LLPS), decreasing the temperature results in the formation of droplets of one liquid phase in the other phase. The temperature at which these droplets are formed is termed the cloud temperature, and may be experimentally determined either by microscopy or by monitoring the transmissibility of the solution. For the experiments described here, the cloud temperature was determined by monitoring the loss in transmissibility at 600 nm as a function of temperature in an Aviv 14DS spectrophotometer (Aviv Biomedical, Lakewood, N.J.). A 5 mm square cuvette was filled with approximately 0.6 mL of the antibody solution. The temperature was decreased from 25° C. to 0° C. in 0.5° C. steps using a thermoelectric chiller. The sample was equilibrated for 10 minutes at each temperature prior to recording the transmission. The cloud temperature was designated as the temperature at which the % transmissibility decreased to 50% of the starting value (Ashcric, 2004). The Tc for anti-IL13 phase separation at different protein concentrations and in different study solutions were measured by using an Aviv Biomedical Model 14S UV-Vis Spectrophotometer. The percent transmittance vs temperature data was collected with a temperature scan from 25° C. to 0° C. at a step size of −0.5° C., equilibration time of 600 seconds, and a wavelength of 600 nm. Measurements of protein solutions were performed in a quartz cuvette with a 1 cm pathlength.

Size Exclusion Chromatography

Size exclusion chromatography was used to quantitate aggregates and fragments. This assay utilized a TSK G3000 SWXL™, 7.8X300 mm column and ran on an HP 1100™ HPLC system at 25° C. Samples were diluted to 2 mg/mL with the mobile phase and injection volume was 25 µL. The mobile phase was 0.2 M $K_2HPO_4$, 0.25 M KCl, at pH 6.2 and the protein was eluted at a steady flow rate of 0.5 mL/min for 30 minutes. The eluent absorbance was monitored at 280 nm. Integration was done using HP CHEMSTATIONM™ software.

Imaged Capillary Isoelectric Focusing (icIEF)

Samples were assayed using icIEF to quantify charge (acidic and basic) variants of anti-IL13 antibody stability samples. This method used a fluorocarbon coated capillary (Convergent Bioscience) in a iCE280 Analyzer (Con vergent Bioscience) with a PrinCE microinjector. Solutions of anolyte and catholyte were purchased from GE Healthcare Biosciences; solutions of pI markers were purchased from Convergent Bioscience).

Capillary Electrpphoresis-Sodium Dodecyl Sulfate (CE-SDS)

CE-SDS was carried out using a Beck man P/ACE MDQ or PA800 capillary electrophoresis system, capable of capillary temperature control from 20 to 40±2° C., with LIF detector at 488 nm excitation.

Anti-IL13 Antibody Potency Assay

The biological activity or potency of anti-IL13 antibody solutions was assessed using a cell culture assay which measured the ability of anti-IL13 antibody solutions to inhibit IL-13 induced luciferase expression in the human bronchial epithelial cell line, L-Beas-2B cells (available from ATCC, ATCC Cat. No. CRL-9609™). Varying concentrations of anti-IL13 antibody standard, control, and samples were mixed with a fixed concentration of IL-13 (e.g., rhu-IL13, Peprotech, Cat. No. 200-13) and added to a 96-well plate seeded with L-Beas-2B cells at a concentration of $2 \times 10^5$ cells/mL. Following incubation, expression of luciferase was quantitated using a luminescent luciferase substrate according to manufacturer's instructions (Bright-Glo™ Luciferase Assay System, Promega Cat. No. E2620, E2650, or Brite-Lite Plus, Perkin Elmer Cat. No. 6016761). Dilution curves for each antibody solution were generated and compared to reference material. The results were expressed in relative luminescence units (RLU). A Relative Potency Estimate was calculated using the method of least squares and a Parallel Line Analysis program. The % Specific Activity was calculated by multiplying the Relative Potency Estimate by the Specific Activity of Reference Material.

Anti-IL13 Antibody (Lebrikizumab) Amino Acid Sequences

The table below shows the amino acid sequences of the CDR-H1, CDR-H2, CDR-H3, CDR-L1, CDR-L2, and CDR-L3 regions of lebrikizumab, along with VH, VL, heavy chain sequences and light chain sequences. As indicated in Table 1 below, VH and the heavy chain may include an N-terminal glutamine and the heavy chain may also include a C-terminal lysine. As is well known in the art, N-terminal glutamine residues can form pyroglutamate and C-terminal lysine residues can be clipped during manufacturing processes.

TABLE 1

| | Anti-IL13 antibody (lebrikizumab) amino acid sequences |
|---|---|
| CDR-H1 (SEQ ID NO.: 1) | Ala Tyr Ser Val Asn |
| CDR-H2 (SEQ ID NO.: 2) | Met Ile Trp Gly Asp Gly Lys Ile Val Tyr Asn Ser Ala Leu Lys Ser |
| CDR-H3 (SEQ ID NO.: 3) | Asp Gly Tyr Tyr Pro Tyr Ala Met Asp Asn |
| CDR-L1 (SEQ ID NO.: 4) | Arg Ala Ser Lys Ser Val Asp Ser Tyr Gly Asn Ser Phe Met His |
| CDR-L2 (SEQ ID NO.: 5) | Leu Ala Ser Asn Leu Glu Ser |
| CDR-L3 (SEQ ID NO.: 6) | Gln Gln Asn Asn Glu Asp Pro Arg Thr |
| VH (SEQ ID NO: 7) | Val Thr Leu Arg Glu Ser Gly Pro Ala Leu Val Lys Pro Thr Gln Thr Leu Thr Leu Thr Cys Thr Val Ser Gly Phe Ser Leu Ser Ala Tyr Ser Val Asn Trp Ile Arg Gln Pro Pro Gly Lys Ala Leu Glu Trp Leu Ala met Ile Trp Gly Asp Gly Lys Ile Val Tyr Asn Ser Ala Leu Lys Ser Arg Leu Thr Ile Ser Lys Asp Thr Ser Lys Asn Gln Val Val Leu Thr Met Thr Asn Met Asp Pro Val Asp Thr Ala Thr Tyr Tyr Cys Ala Gly Asp Gly Tyr Tyr Pro Tyr Ala Met Asp Asn Trp Gly Gln Gly Ser Leu Val Thr Val Ser Ser |
| VH (SEQ ID NO: 8) | Gln Val Thr Leu Arg Glu Ser Gly Pro Ala Leu Val Lys Pro Thr Gln Thr Leu Thr Leu Thr Cys Thr Val Ser Gly Phe Ser Leu Ser Ala Tyr Ser Val Asn Trp Ile Arg Gln Pro Pro Gly Lys Ala Leu Glu Trp Leu Ala Met Ile Trp Gly Asp Gly Lys Ile Val Tyr Asn Ser Ala Leu Lys Ser Arg Leu Thr Ile Ser Lys Asp Thr Ser Lys Asn Gln Val Val Leu Thr Met Thr Asn Met Asp Pro Val Asp Thr Ala Thr Tyr Tyr Cys Ala Gly Asp Gly Tyr Tyr Pro Tyr Ala met Asp Asn Trp Gly Gln Gly Ser Leu Val Thr Val Ser Ser |
| VL (SEQ ID NO: 9) | Asp Ile Val Met Thr Gln Ser Pro Asp Ser Leu Ser Val Ser Leu Gly Glu Arg Ala Thr Ile Asn Cys Arg Ala Ser Lys Ser Val Asp Ser Tyr Gly Asn Ser Phe Met His Trp Tyr Gln Gln Lys Pro Gly Gln Pro Pro Lys Leu Leu Ile Tyr Leu Ala Ser Asn Leu Glu Ser Gly Val Pro Asp Arg Phe Ser Gly Ser Gly Ser Gly Thr Asp Phe Thr Leu Thr Ile Ser Ser Leu Gln Ala Glu Asp Val Ala Val Tyr Tyr Cys Gln Gln Asn Asn Glu Asp Pro Arg Thr Phe Gly Gly Gly Thr Lys Val Glu Ile Lys Arg |
| H Chain (SEQ ID NO.: 10) | VTLRESGPA LVKPTQTLTL TCTVSGFSLS AYSVNWIRQP PGKALEWLAM IWGDGKIVYN SALKSRLTIS KDTSKNQVVL TMTNMDPVDT ATYYCAGDGY YPYAMDNWGQ GSLVTVSSAS TKGPSVFPLA PCSRSTSEST AALGCLVKDY FPEPVTVSWN SGALTSGVHT FPAVLQSSGL YSLSSVVTVP SSSLGTKTYT CNVDHKPSNT KVDKRVESKY GPPCPPCPAP EFLGGPSVFL FPPKPKDTLM ISRTPEVTCV VVDVSQEDPE VQFNWYVDGV EVHNAKTKPR EEQFNSTYRV VSVLTVLHQD WLNGKEYKCK VSNKGLPSSI EKTISKAKGQ PREPQVYTLP PSQEEMTRNQ VSLTCLVKGF YPSDIAVEWE SNGQPENNYK TTPPVLDSDG SFFLYSRLTV DKSRWQEGNV FSCSVMHEAL HNHYTQKSLS LSLG |
| H Chain (SEQ ID NO: 11) | QVTLRESGPA LVKPTQTLTL TCTVSGFSLS AYSVNWIRQE PGKALEWLAM IWGDGKIVYN SALKSRLTIS KDTSKNQVVL TMTNMDPVDT ATYYCAGDGY YPYAMDNWGQ GSLVTVSSAS TKGPSVFPLA PCSRSTSEST AALGCLVKDY FPEPVTVSWN SGALTSGVHT FPAVLQSSGL YSLSSVVTVP SSSLGTKTYT CNVDHKPSNT KVDKRVESKY GPPCPPCPAP EFLGGPSVFL FPPKPKDTLM ISRTPEVTCV VVDVSQEDPE VQFNWYVDGV EVHNAKTKPR EEQFNSTYRV VSVLTVLHQD WLNGKEYKCK VSNKGLPSSI EKTISKAKGQ PREPQVYTLP |

TABLE 1-continued

Anti-IL13 antibody (lebrikizumab) amino acid sequences

```
              PSQEEMTKNQ VSLTCLVKGF YPSDIAVEWE SNGQPENNYK TTPPVLDSDG
              SFFLYSRLTV DKSRWQEGNV FSCSVMHEAL HNHYTQKSLS LSLG

H Chain       VTLRESGPA LVKPTQTLTL TCTVSGFSLS AYSVNWIRQP PGKALEWLAM
(SEQ ID       IWGDGKIVYN SALKSRLTIS KDTSKNQVVL TMTNMDPVDT ATYYCAGDGY
NO.: 12)      YPYAMDNWGQ GSLVTVSSAS TKGPSVFPLA PCSRSTSEST AALGCLVKDY
              FPEPVTVSWN SGALTSGVHT FPAVLQSSGL YSLSSVVTVP SSSLGTKTYT
              CNVDHKPSNT KVDKRVESKY GPPCPPCPAP EFLGGPSVFL FPPKPKDTLM
              ISRTPEVTCV VVDVSQEDPE VQFNWYVDGV EVHNAKTKPR EEQFNSTYRV
              VSVLTVLHQD WLNGKEYKCK VSNRGLPSSI EKTISKAKGQ PREPQVYTLP
              PSQEEMTKNQ VSLTCLVKGF YPSDIAVEWE SNGQPENNYK TTPPVLDSDG
              SFFLYSRLTV DKSRWQEGNV FSCSVMHEAL HNHYTQKSLS LSLGK H Chain       QVTLRESGPA LVKPTQTLTL TCTVSGFSLS AYSVNWIRQP PGKALEWLAM
(SEQ ID       IWGDGKIVYN SALKSRLTIS KDTSKNQVVL TMTNMDPVDT ATYYCAGDGY
NO.: 13)      YPYAMDNWGQ GSLVTVSSAS TKGPSVFPLA PCSRSTSEST AALGCLVKDY
              FPEPVTVSWN SGALTSGVHT FPAVLQSSGL YSLSSVVTVP SSSLGTKTYT
              CNVDHKPSNT KVDKRVESKY GPPCPPCPAP EFLGGPSVFL FPPKPKDTLM
              ISRTPEVTCV VVDVSQEDPE VQFNWYVDGV EVHNAKTKPR EEQFNSTYRV
              VSVLTVLHQD WLNGKEYKCK VSNKGLPSSI EKTISKAKGQ PREPQVYTLP
              PSQEEMTKNQ VSLTCLVKGF YPSDIAVEWE SNGQPENNYK TTPPVLDSDG
              SFFLYSRLTV DKSRWQEGNV FSCSVMHEAL HNHYTQKSLS LSLGK L Chain       DIVMTQSTDS LSVSLGERAT INCRASKSVD SYGNSFMHWY QQKPGQPPKL
(SEQ ID       LIYLASNLES GVPDRFSGSG SGTDFTLTIS SLQAEDVAVY YCQQNNEDPR
NO.: 14)      TFGGGTKVEI KRTVAAPSVF IFPPSDEQLK SGTASVVCLL NNFYPREAKV
              QWKVDNALQS GNSQESVTEQ DSKDSTYSLS STLTLSKADY EKHKVYACEV
              THQGLSSPVT KSFNRGEC
```

Results

Physical and Chemical Stability of Anti-IL13 Antibody Formulations at Various pH Buffers with varying pH were made using either 20 mM histidine acetate or 20 mM sodium phosphate to cover the pH range 5.4-7.8. The histidine acetate buffers covered the pH range of 5.4-6.0 and the sodium phosphate buffers covered the pH range of 6.6-7.8. For each buffer pH, the following were held constant: anti-IL13 antibody concentration at 150 mg/ml, 175 mM sucrose and 0.3 mg/mL (0.03%) polysorbate 20.

Antibody solutions were stored in vials for the time periods and at the temperatures indicated in Table 2 below. At various times, indicated by "X" in Table 2, samples were assayed by various methods to assess physical stability, including SEC, A350 turbidity and non-reducing CE-SDS, and chemical stability, including icIEF.

TABLE 2

Stability timepoints and conditions used to determine physical and chemical stability anti-IL13 antibody solutions.

| Temperature | Weeks at Storage Condition week | | | | | | |
|---|---|---|---|---|---|---|---|
| | 0 | 1 | 2 | 4 | 6 | 8 | 12 |
| −70° C. | X | | | | | | |
| 2-8° C. | | | | | X | | X |
| 30° C. | | X | X | X | X | X | X |

FIG. 1 shows the percent monomer loss per week in buffers at the indicated pH as determined by SEC. As shown in FIG. 1, % monomer loss was lower in the lower pH range than in the higher pH range, with the lowest % monomer loss at pH 5.7, which showed a % monomer loss/week of 0.056.

Figure 2:
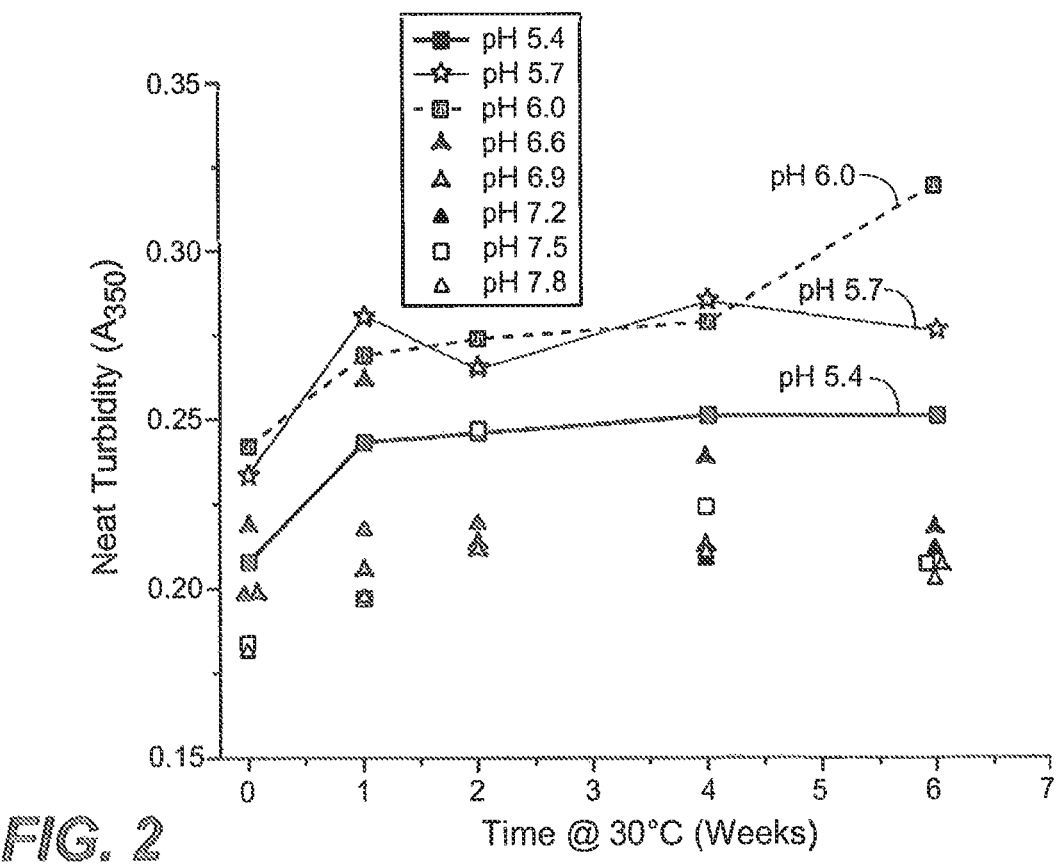
FIG. 2 shows increases in solution turbidity at 350 nm of anti-IL13 antibody solutions as a function of pH during storage at 30° C. as described in Example 1.

Another physical stability assay measured changes in turbidity (as determined by A350) over time at 30° C. as a function of pH. As shown in FIG. 2, the initial turbidities and changes are higher for the buffers between pH5.4-6.0 than at the higher pH ranges. In FIG. 2, neat turbidity is A350=1/T where T is transmitted light intensity at 350 nm with a specified path length of 1 cm.

Figure 3:
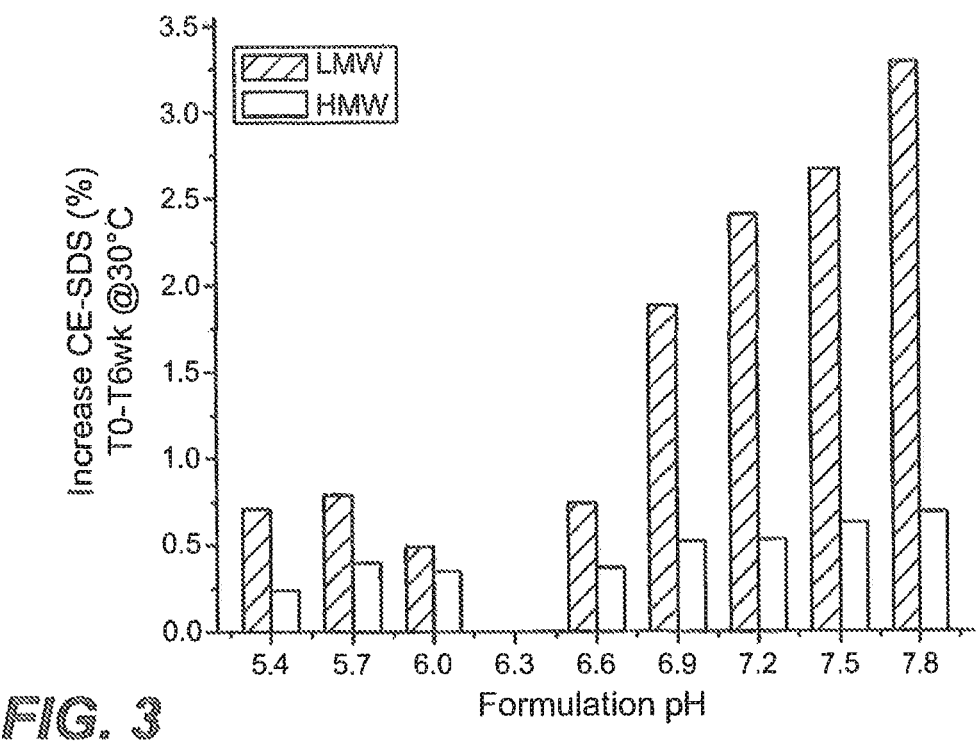
FIG. 3 shows changes in low molecular weight (LMW) soluble fragments and high molecular weight (HMW) aggregates measured by non-reduced CE-SDS during storage at 30° C. as a function of pH as described in Example 1.

A third physical stability assay measured increases in low molecular weight (LMW) soluble fragments and high molecular weight (HMW) aggregates in anti-IL13 antibody solutions during six weeks of storage at 30° C. as a function of pH. As shown in FIG. 3, fragmentation rates and aggregation rates were lowest in the lower pH range, pH 5.4-6.6.

Figure 4:
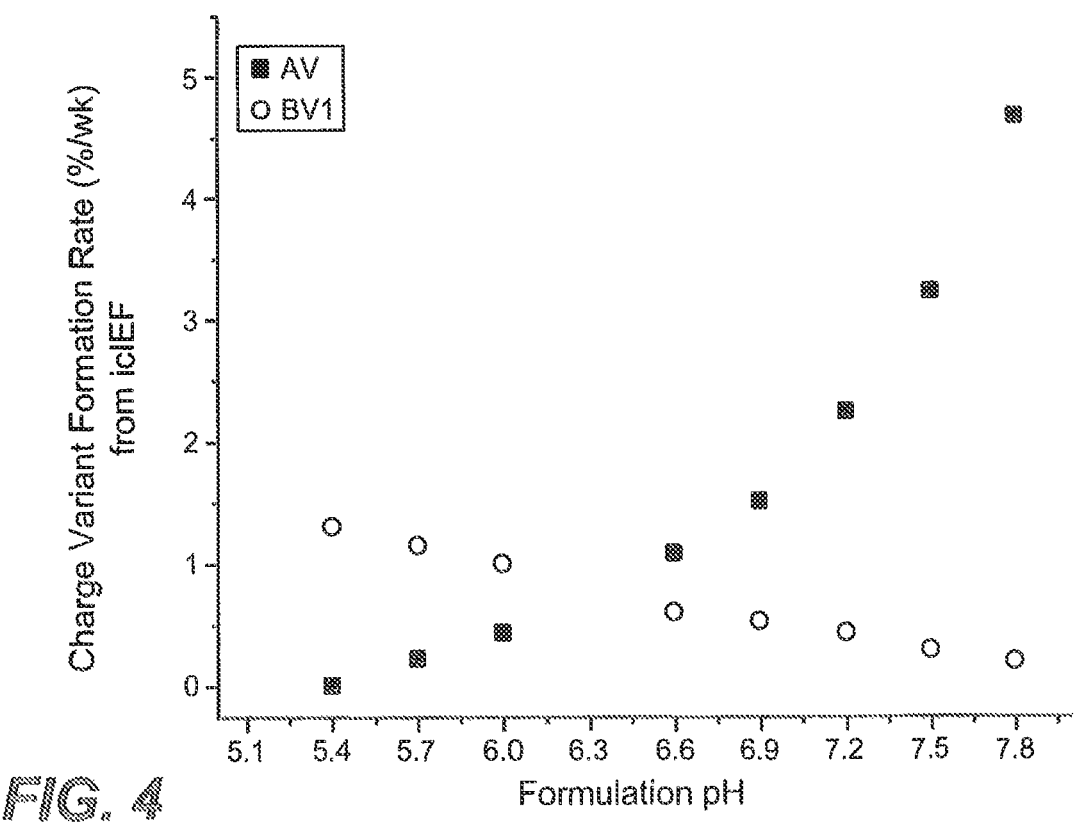
FIG. 4 shows the rates of acidic variants (AV) and basic variant (peak 1) (BV) formation at 30° C. as a function of pH as described in Example 1. Charge valiant formation rate is expressed as %/week shown on the vertical axis.
Figure 5:
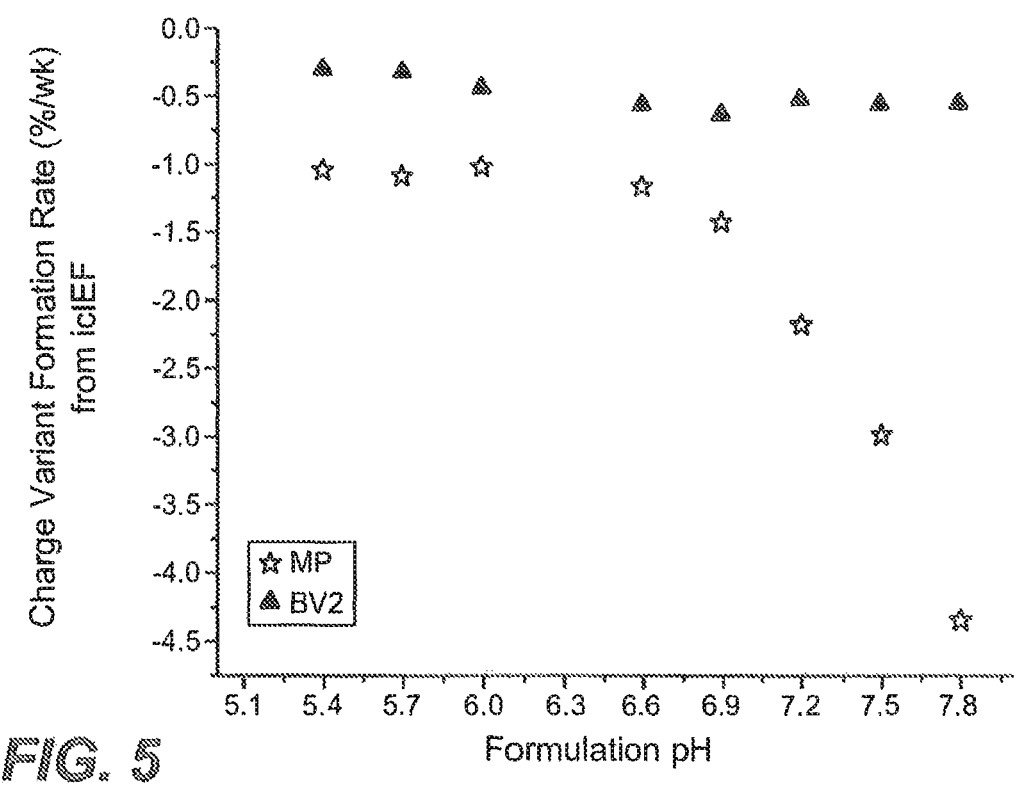
FIG. 5 shows the rates of basic variant (peak 2) (BV2) formation and main peak (MP) loss at 30° C. as a function of pH as described in Example 1. Charge variant formation rate is expressed as %/week shown on the vertical axis.

We also assessed chemical stability using icIEF to determine changes in the rate of acidic and basic variant formation over time at 30° C. as a function of pH (FIG. 4) and changes in the rate of basic variant and main peak loss over time at 30° C. as a function of pH (FIG. 5). As shown in FIG. 4, the rate of acidic variant was lowest in the low pH range and highest in the high pH range, while the rate of basic variant (BV1 peak) was lowest in the high pH range and highest in the low pH range. The results shown in FIG. 5 indicate that main peak loss was minimized between pH 5.4-6.0.

Figure 6:
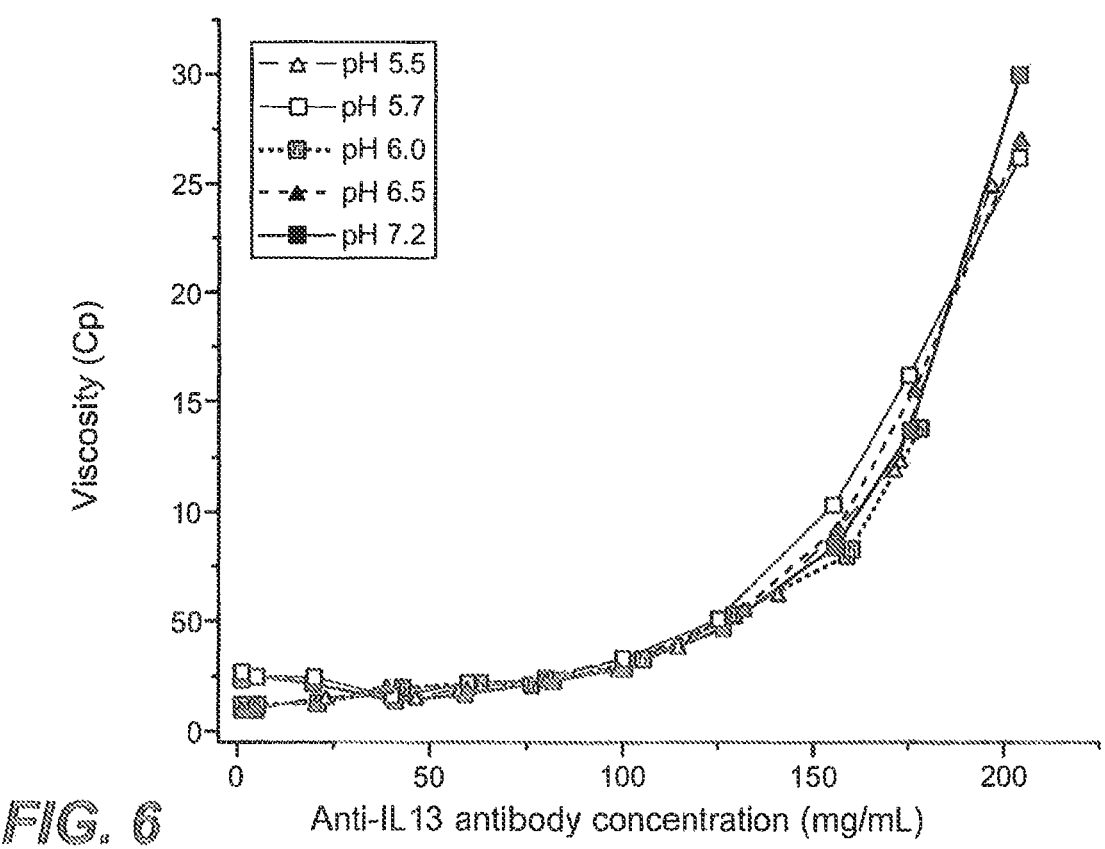
FIG. 6 shows a rheological characterization of anti-IL13 antibody as a function of antibody concentration and solution pH as described in Example 1. Solution viscosity is expressed, in centipoise (cP) at 25° C. shown on the vertical axis.

To determine whether pH affected solution viscosity, we performed rheological characterization of different anti-IL13 antibody concentrations (ranging from 0 to 200 mg/mL antibody) at varying pH (ranging from pH 5.5-7.2). Each solution had 175 mM sucrose and 0.3 mg/mL polysorbate 20. The results are shown in FIG. 6. Those results indicate that a consistent viscosity profile was maintained regardless of solution pH for a given antibody concentration. In particular, the results showed that viscosity at higher antibody concentrations were not influenced by pH.

Taken together, the data presented in FIGS. 1-6 show that there was a shallow gradient for most physical and chemical changes at pH 5.4-6.0. The 20 mM histidine acetate buffer at pH 5.7 was therefore chosen for subsequent studies and formulation assessment.

Figure 7:
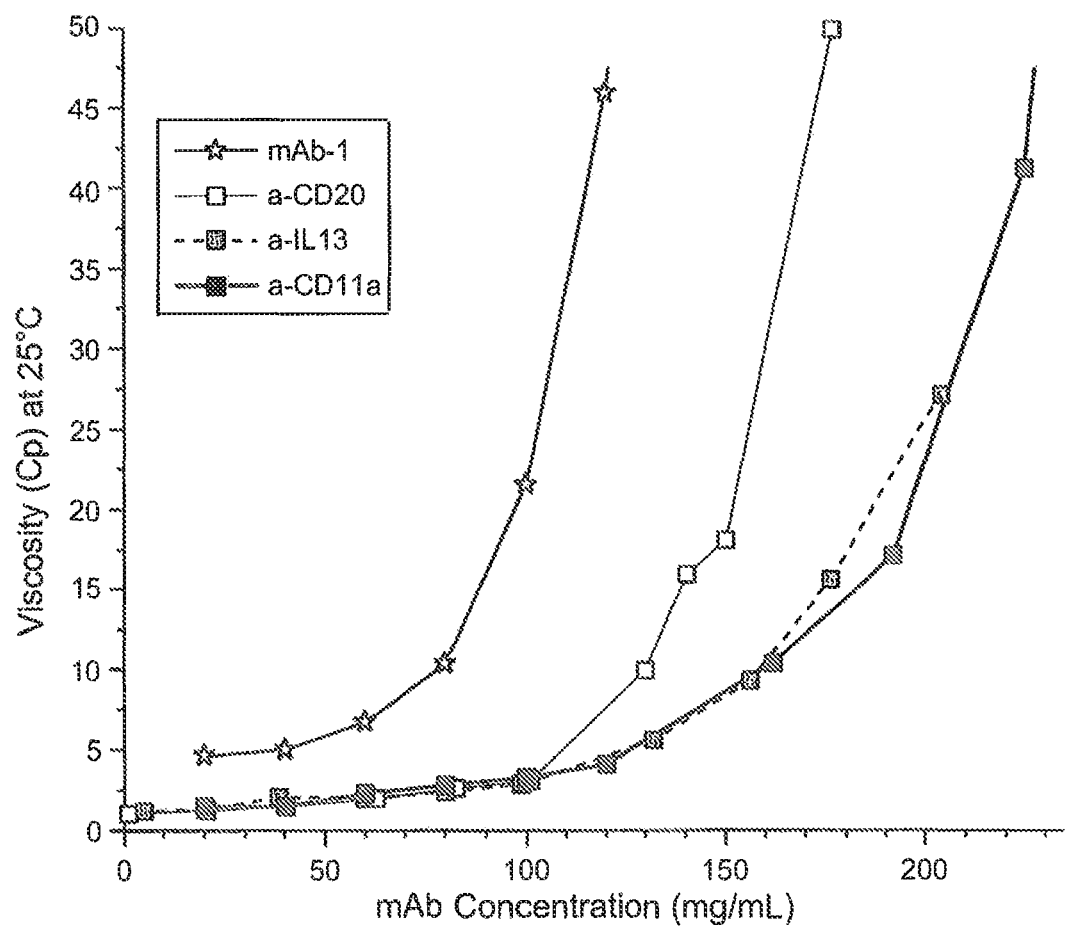
FIG. 7 shows a rheological characterization of different monoclonal antibodies over a wide range of concentrations as described in Example 1. Solution viscosity is expressed in centipoise (cP) at 25° C. shown on the vertical axis.

Rheological Characterization of High Concentration Monoclonal Antibody Solutions To explore whether the viscosity observed (<15 cP at 25° C.) for the anti-IL13 antibody formulated at 150 mg/mL in 20 mM histidine acetate pH 5.7, 175 mM sucrose, 0.3 mg/mL polysorbate 20 would be generally observed for various different antibodies, we tested the viscosity of three additional antibodies in similar formulations at 150 mg/mL. Such a viscosity profile as observed for the anti-IL13 antibody is desirable for manufacturing at high antibody concentration and for certain routes of drag administration, for example, subcutaneous injection. As shown in FIG. 7, anti-IL13 antibody maintained a viscosity profile similar to the anti-CD11a antibody with viscosity of <15 cP at 25° C. In contrast, the anti-CD20 antibody and the mAb-1 antibody showed quite different viscosity profiles. The viscosity of the anti-CD20 antibody at 150 mg/mL was >15 cP at 25° C., while mAb-1 could not be formulated at 150 mg/mL in this buffer formulation due to significant problems with viscosity as can be seen in FIG. 7. FIG. 7 shows that the viscosity of mAb-1 at 125 mg/mL was >45 cP at 25° C. Accordingly, it is clear from this data the different antibodies have different rheological characteristics when formulated at 150 mg/mL in 20 mM histidine acetate pH 5.7, 175 mM sucrose, 0.3 mg/mL polysorbate 20.

Characterization of Visual Appearance and Opalescence

Figure 8:
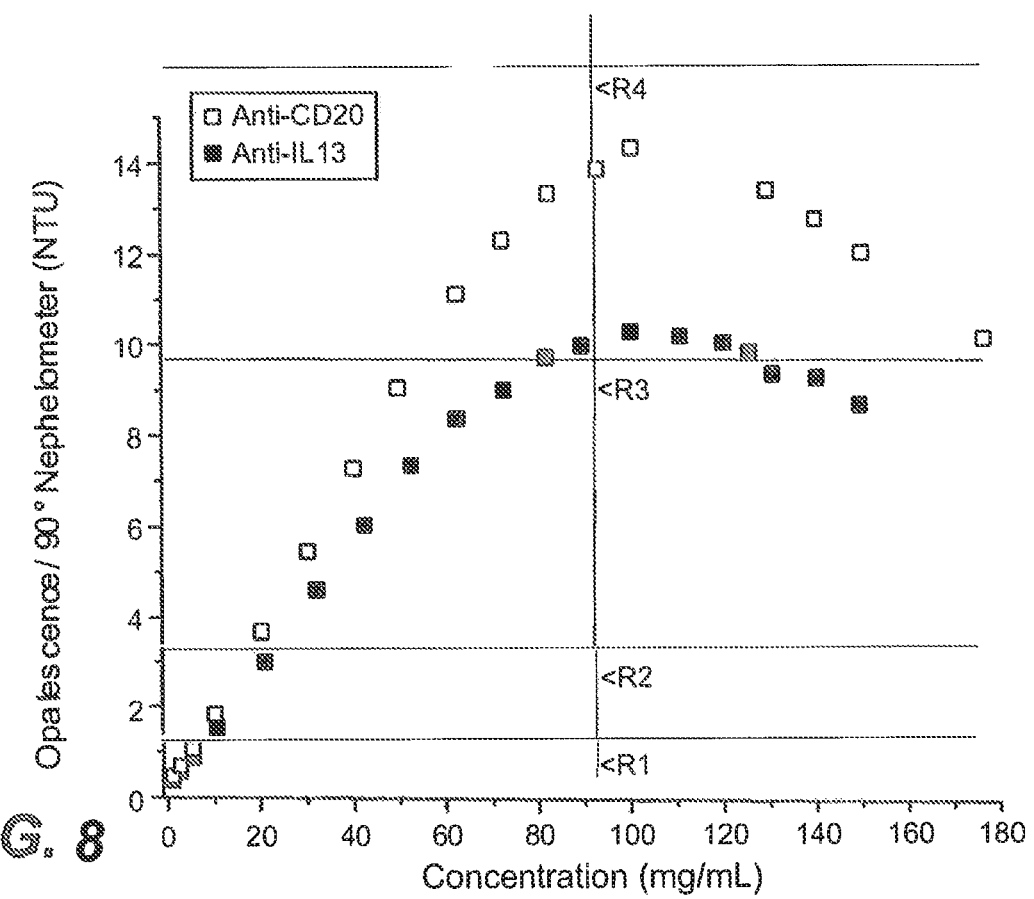
FIG. 8 shows the quantification of visual appearance of anti-XL13 and anti-CD20 antibody solutions as a function of concentration using 90 degree nephelometry as described in Example 1.
Figure 9:
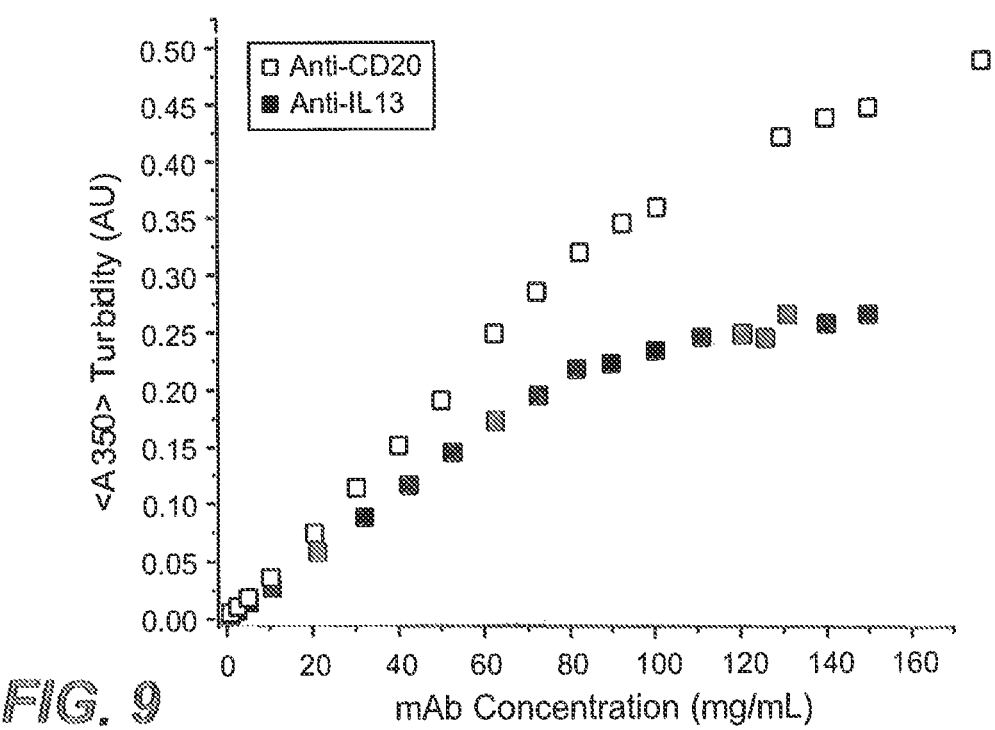
FIG. 9 shows turbidity measurements (A350) for anti-IL13 and anti-CD20 antibody solutions as a function of mAb concentration as described in Example 1.

We characterized the visual appearance and opalescence of the anti-IL13 antibody formulation in comparison to an anti-CD20 antibody formulation using 90 degree nephelometry and measurements of A350 turbidity. FIG. 8 shows the quantification of visual appearance of the two different antibody formulations in nephelometric turbidity units (NTU). In FIG. 8, R1, R2, R3, and R4 refer to reference standards with R4 having the highest degree of visual opalescense and R1 having the lowest. The measurements of A350 turbidity for the anti-IL13 and anti-CD20 antibodies are shown in FIG. 9. As shown in FIG. 9, for each antibody formulation, turbidity increased with increasing protein concentration. The results shown in these figures demonstrate that two different measurements of visual appearance for two antibodies have different trends, especially at higher protein concentrations due to differences in what is intrinsically measured. The data also show that the measurement trends are consistent between these two antibodies which appear to have elevated solution opalescence.

Figure 10:
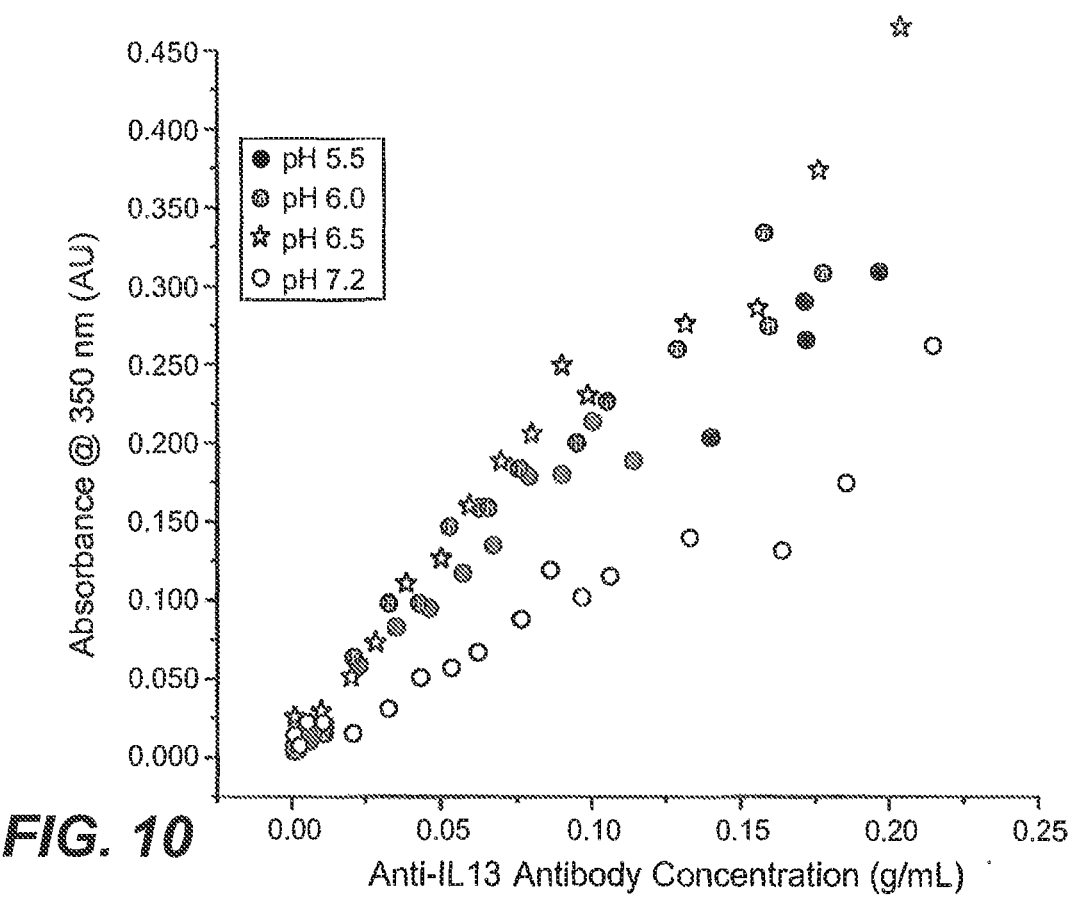
FIG. 10 shows anti-IL13 antibody solution turbidity as a function of concentration and pH as described in Example 1.

We also examined anti-IL13 antibody concentration as a function of concentration and pH. The results are shown in FIG. 10. Solutions showing the greatest turbidity were in the vicinity of the mAb isoelectric point (pI).

While not being bound by theory, we interpret these results to indicate that the absorbance at 350 nm wavelength (turbidity) increased with increasing protein concentration due to the absorption of light by the protein absorption band, with maxima around 280 nm due to the broad tail of this peak. A second contributing factor to the increased A350 vs concentration of mAb solutions was the non-linear increase in light scattering, reducing the total transmitted light.

Figure 11:
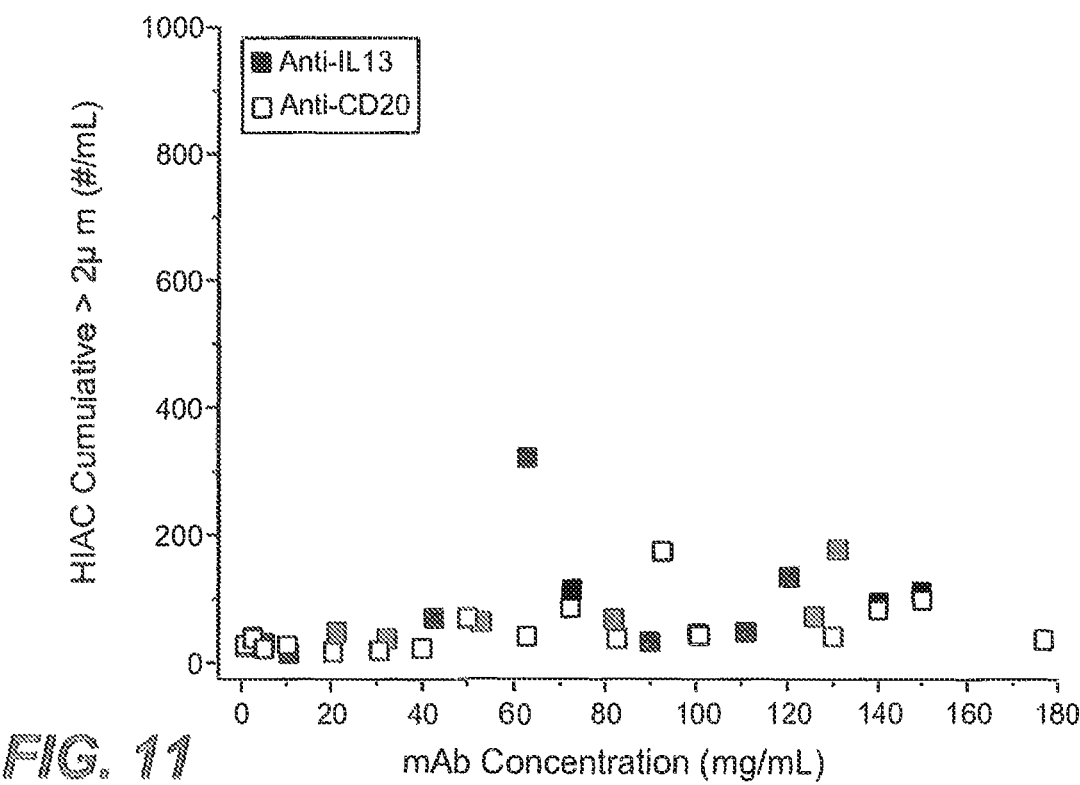
FIG. 11 shows subvisible particulate counts in anti-IL13 and anti-CD20 antibody solutions as a function of mAb concentration as described in Example 1.
Figure 12:
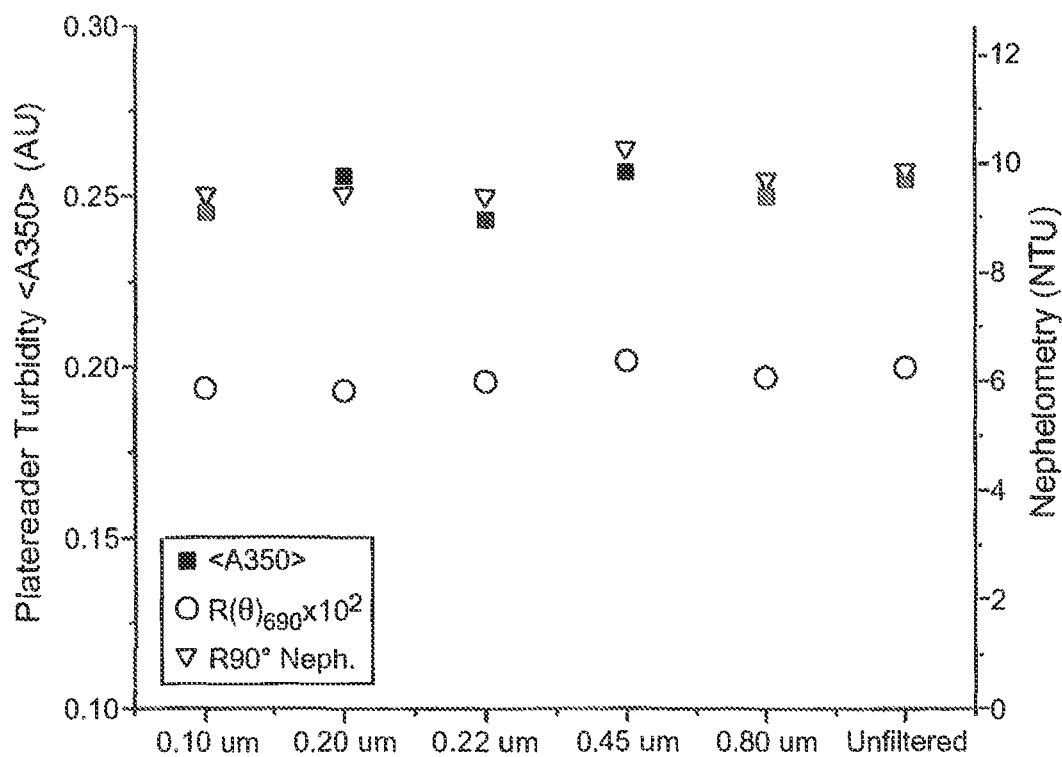
FIG. 12 shows measurements of nephelometric, turbidimetric, and static light scattering of 125 mg/mL solution of anti-IL13 antibody as described in Example 1.

In addition, we assessed subvisible particle counts as a function of mAb concentration and those results are shown in FIG. 11. No significant increase in subvisible particulate >2 µm in size was observed by HIAC light obscuration analysis indicating that particulate matter >2 µm does not contribute to the opalescence or turbidity of anti-IL13 antibody solutions. FIG. 12 shows measurements of nephelometric, turbidimetric and static light scattering of 125 mg/mL solution of anti-IL13 antibody when the antibody solutions were filtered with increasingly small pore sizes (down to 0.1 µm or 100 nm). These results shown in FIGS. 11 and 12 collectively indicate that the anti-IL13 antibody solution and drug product formulation appearance are not determined by subvisible or submicron particulate matter inducing concentration dependence of light scattering.

Figure 13:
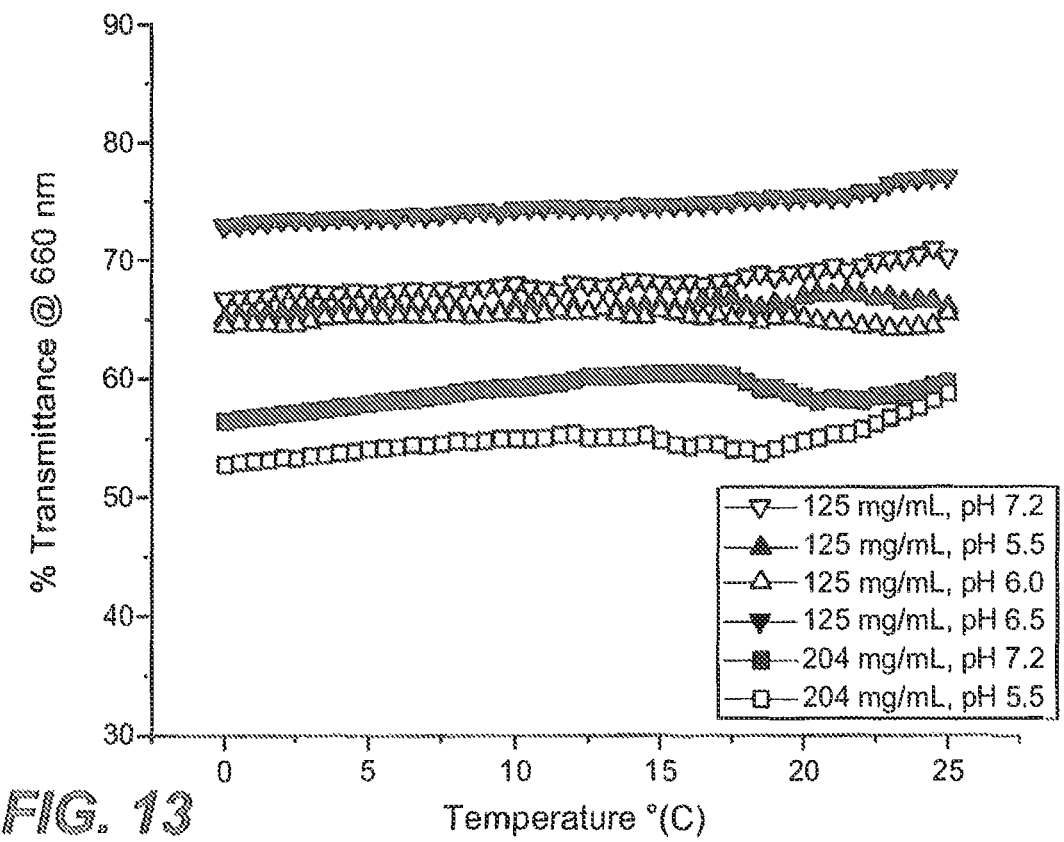
FIG. 13 summarizes the temperature dependence of solution opalescence at different pH conditions for anti-IL13 antibody at 125 mg/mL and at 204 mg/mL as described in Example 1.

Next, we investigated the dependence of solution appearance as a function of solution pH at 125 mg/mL and 204 mg/mL. Solution appearance was assessed using a temperature scan of the transmitted light intensity at 600 nm. The results are shown in FIG. 13 and indicate that anti-IL13 antibody solution opalescence, which remained constant as a function of decreasing temperature, was not due to critical phenomena such as liquid-liquid phase separation, where solution components have divergent solubility and form two separate phases of distinct composition. This suggests that solution homogeneity (phase separation) across a range of typical storage and/or exposure temperatures is not influenced by temperature despite the initial solution opalescence/visual appearance (at room temperature).

Thermal Stability ($T_{melt}$) Studies

Figure 14:
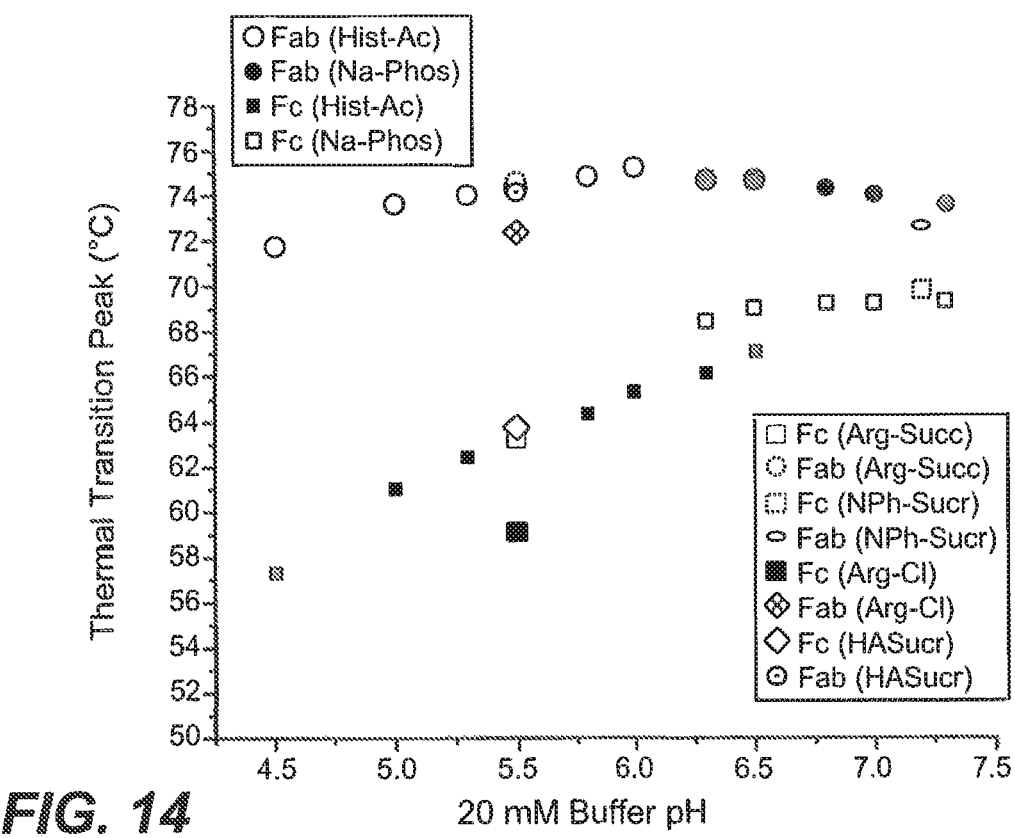
FIG. 14 summarizes the thermal melting transition peaks observed for two partially resolved peaks in the capillary DSC as a function anti-IL13 formulation composition and solution pH as described in Example 1.

We measured the thermal melting transition peaks for two partially resolved peaks in the capillary differential scanning calorimeter as a function of formulation composition and solution pH. The results are shown in FIG. 14. As shown in FIG. 14, a maxima in melting transition behavior for anti-IL13 as a function of pH was observed between pH 6.0-7.5. The prevailing scientific opinion is that the lower the melting transition occurs, the lower the expected physical stability of the system upon storage for any duration. See, e.g., Chi et al., Protein Science 12(5):903-913 (2003); Chi et al., Pharmaceutical Research 20(9): 1325-1336 (2003); Goldberg et al., J. Pharm. Sciences 100(4): 1306-1315 (2011). Thus, the physical stability data shown herein for the anti-IL13 antibody formulation (pH 5.7) was surprising and unexpected.

Colloidal Stability

Colloidal stability was measured by static light scattering using dilute solutions of antibody (between 0.10-1 mg/mL) as well as light scattering at antibody concentrations exceeding 200 mg/mL. Colloidal stability refers to the solution behavior of macromolecules suspended in solution, and allows one to investigate the equilibrium, time averaged interactions between macromolecules such as monoclonal antibodies. Without being bound by theory, when interactions are repulsive, then the solution composition can be expected to remain stable. Net attractive interactions between solute molecules occur, however, and are generally associated with phase transitions and protein solubility problems.

Figure 15:
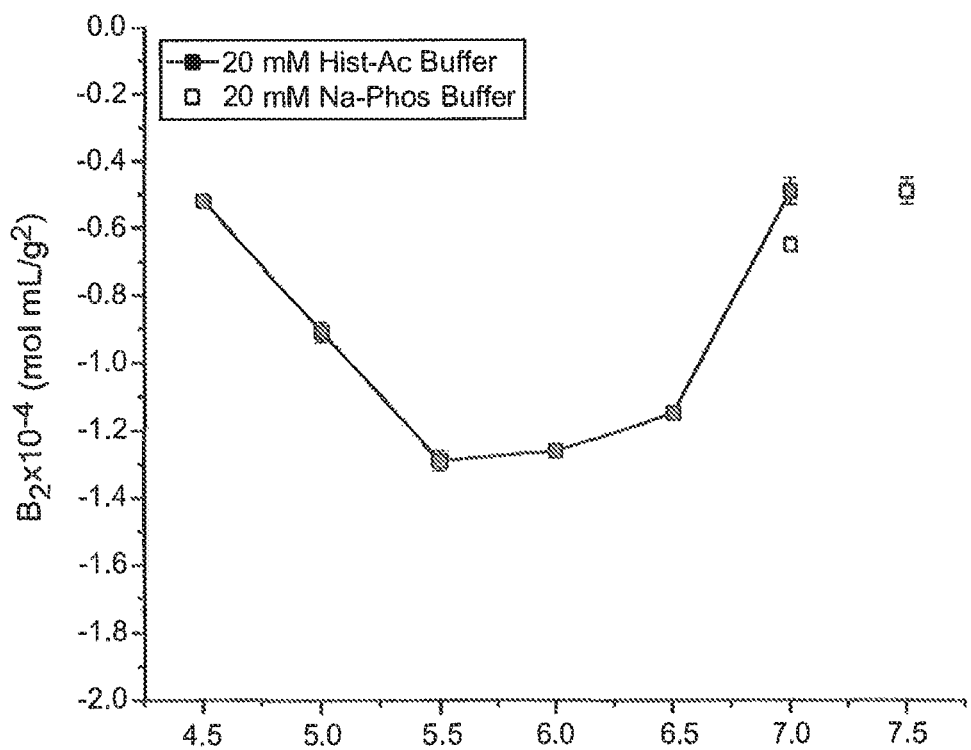
FIG. 15 summarizes the measured osomotic second virial coefficients ($B_2$) for anti-IL13 antibody as a function of solution pH with samples in simple buffers as indicated and measured from 0.1-1.0 mg/mL as described in Example 1.
Figure 16:
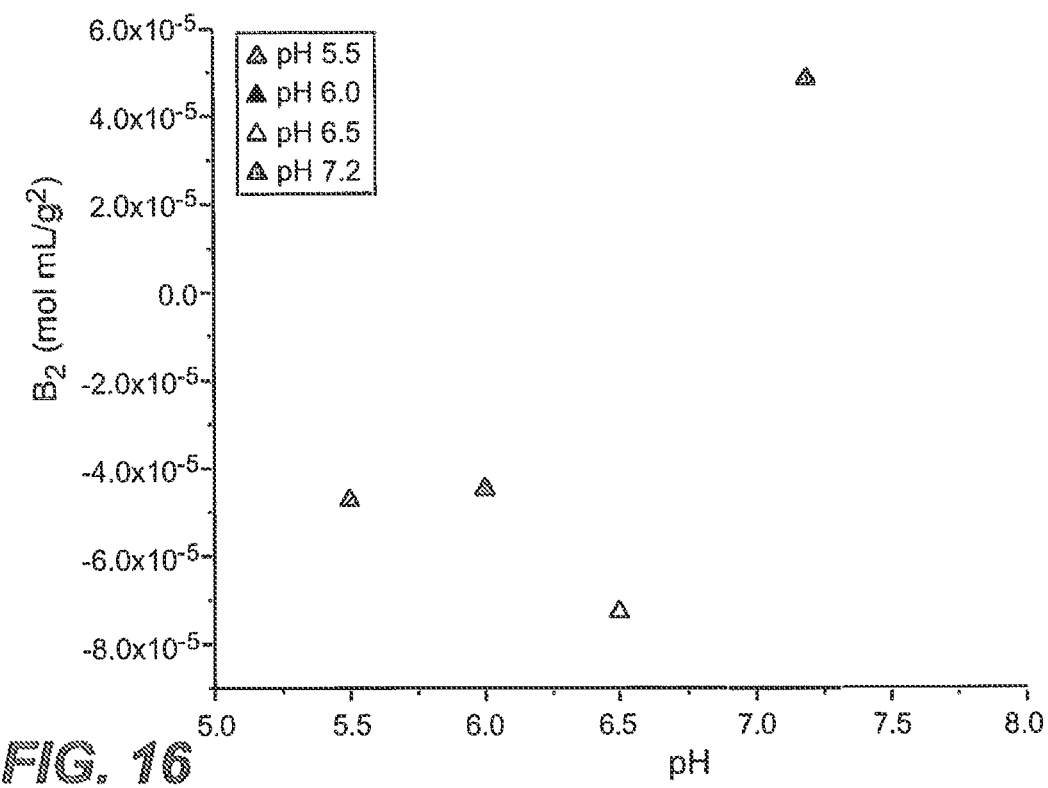
FIG. 16 shows the measured osmotic second virial coefficients for anti-IL13 antibody as a function of formulation composition and pH over the range of 1.0-10 mg/mL as described in Example 1.
Figure 17:
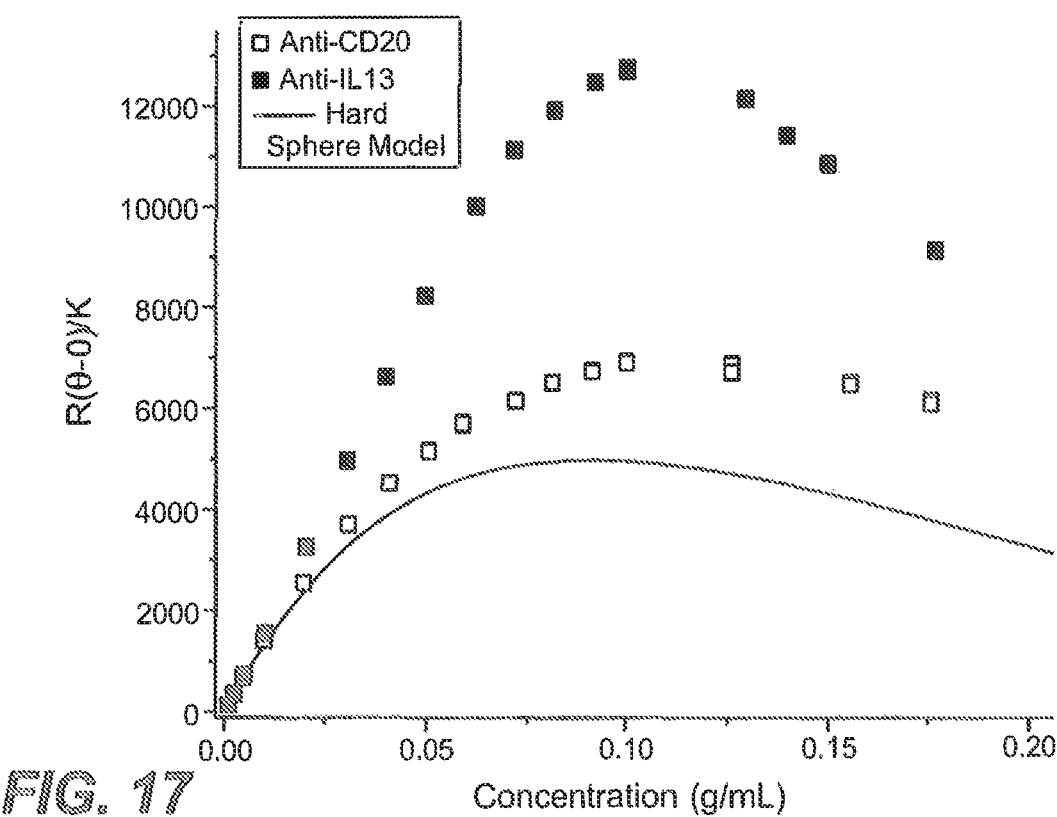
FIG. 17 shows the measured static light scattering intensity vs. concentration for each of the anti-IL13 and anti-CD20 antibodies in comparison to the hard sphere (HS) model as described in Example 1.

We measured osmotic second virial coefficients ($B_2$) for anti-IL13 antibody (at concentrations ranging from 0.1 to 1.0 mg/mL) as a function of solution pH with samples in simple buffers. Note that in FIGS. 15 and 16, values above 0 are positive osmotic second virial coefficients which indicate net repulsive interactions and values below 0 are negative osmotic second virial coefficients which indicate net attractive intermolecular interactions. The data in FIG. 15 shows that anti-IL13 antibody had attractive interactions across the pH range, but that the strongest attractive interactions occurred between pH 5.5-6.5. For the results shown in FIG. 16, formulation additives were added to the solutions at different pHs. As can be seen in FIG. 16, the measured osmotic second virial coefficients at pH 5.5-6.5 remained negative and therefore attractive. Measurements of light scattering with a multi-angle light scattering detector across the range of concentrations 1-200 mg/mL extrapolating intensities to scattering angle of 0 are shown in FIG. 17.

Figure 18:
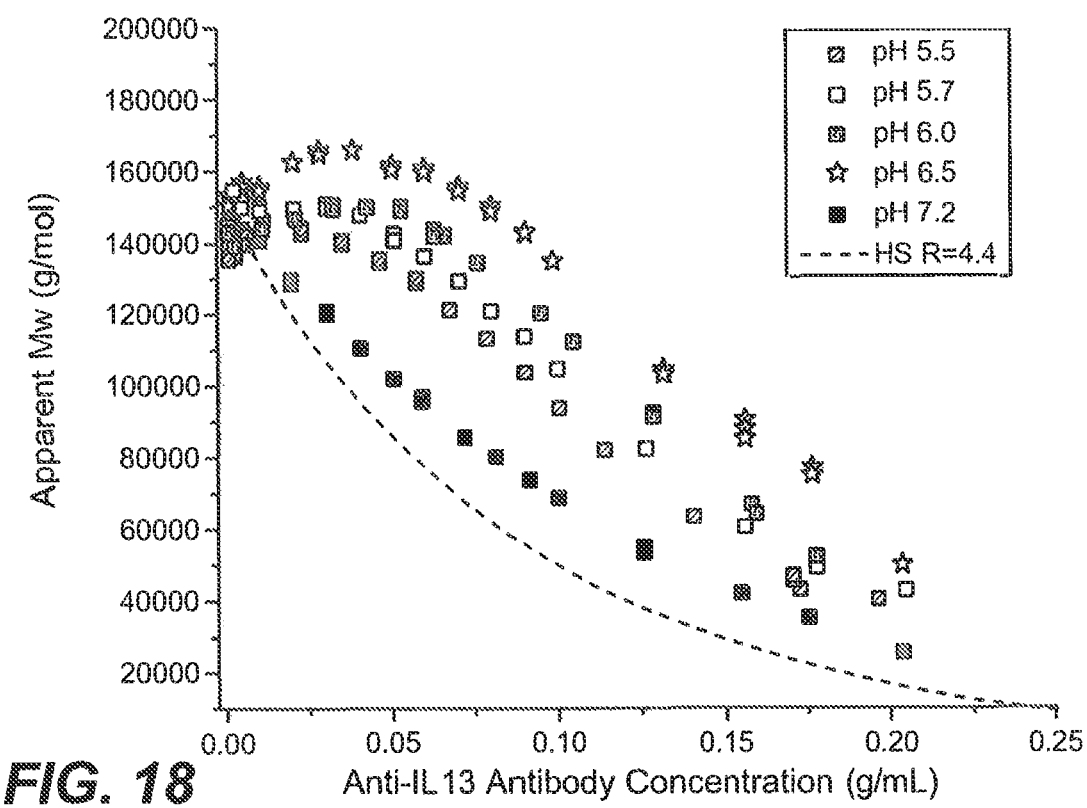
FIG. 18 shows static light, scattering data for anti-IL13 antibody as a function of formulation pH represented as apparent molecular weights observed at concentrations up to 200 mg/mL as described in Example 1.

These data revealed that the scattered intensity profile was highly similar to that observed for the HACH nephelometer (compare FIG. 8 to FIG. 17). Both instruments measure the scattered light intensity, and therefore the Rayleigh scattering. This scattering dominates in solutions free of particulates and is caused by small density and concentration fluctuations of the solution that are also dependent on the interactions between the scattering molecules. The decrease in scattered light intensity occurs when the molecules are increasingly in close contact with one another and their positions in time/space become correlated resulting in destructive interference of scattered light (See, e.g., Bettelheim et al., *Biophysical Journal* 41(1): 29-33 (1983); Xia et al., Biophysical Journal 66(3_JP_1): 861-872 (1994); and Xia et al., *Biophysical Journal* 41(1): 29-33 (1996). FIG. 18 shows static light scattering data for anti-IL13 antibody as a function of formulation pH. The data in FIG. 18 are represented as apparent molecular weights observed at antibody concentrations up to 200 mg/mL. The data shown in FIG. 18 indicated weak (pH 7.2) to moderately attractive colloidal (pH 6.5) interactions and anti-IL13 antibody self-association across the concentration range, relative to the theoretical scattering for a simple hard sphere species model of mAb excluded volume (dashed line in FIG. 18).

Figure 19:
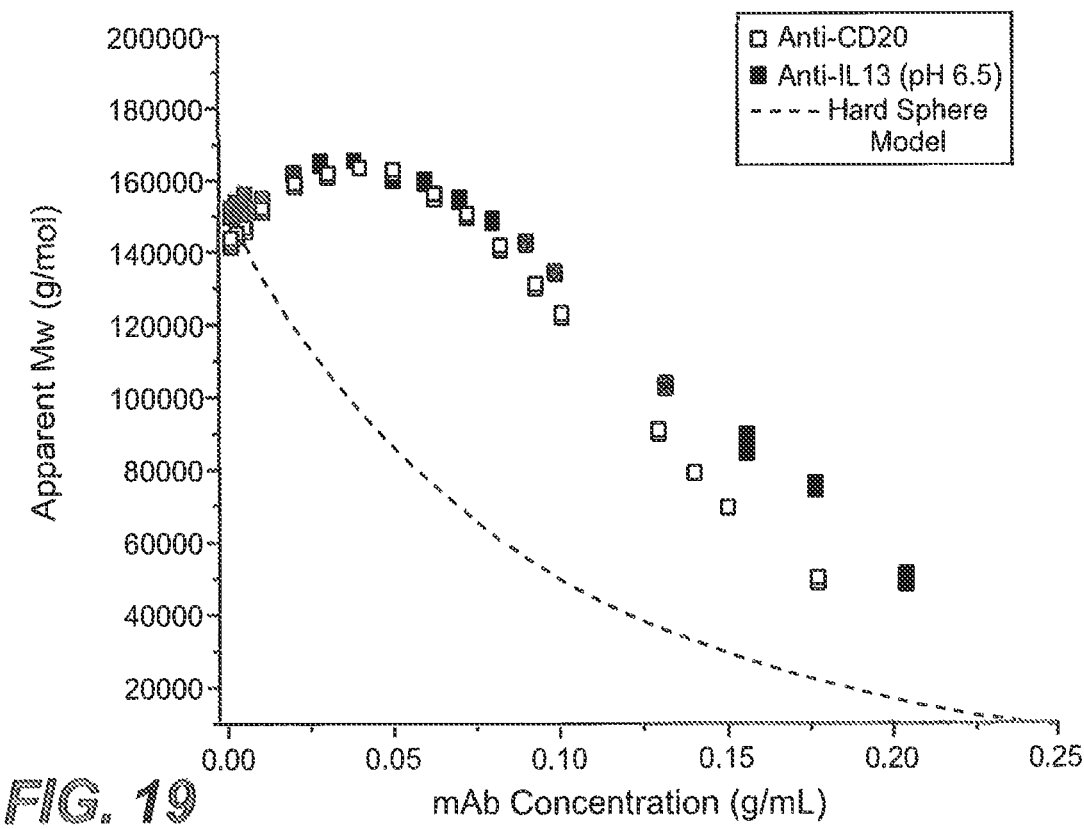
FIG. 19 shows the apparent molecular weights of anti-IL13 and anti-CD20 antibodies in solution at high concentrations up to 200 mg/mL as described in Example 1.
Figure 20:
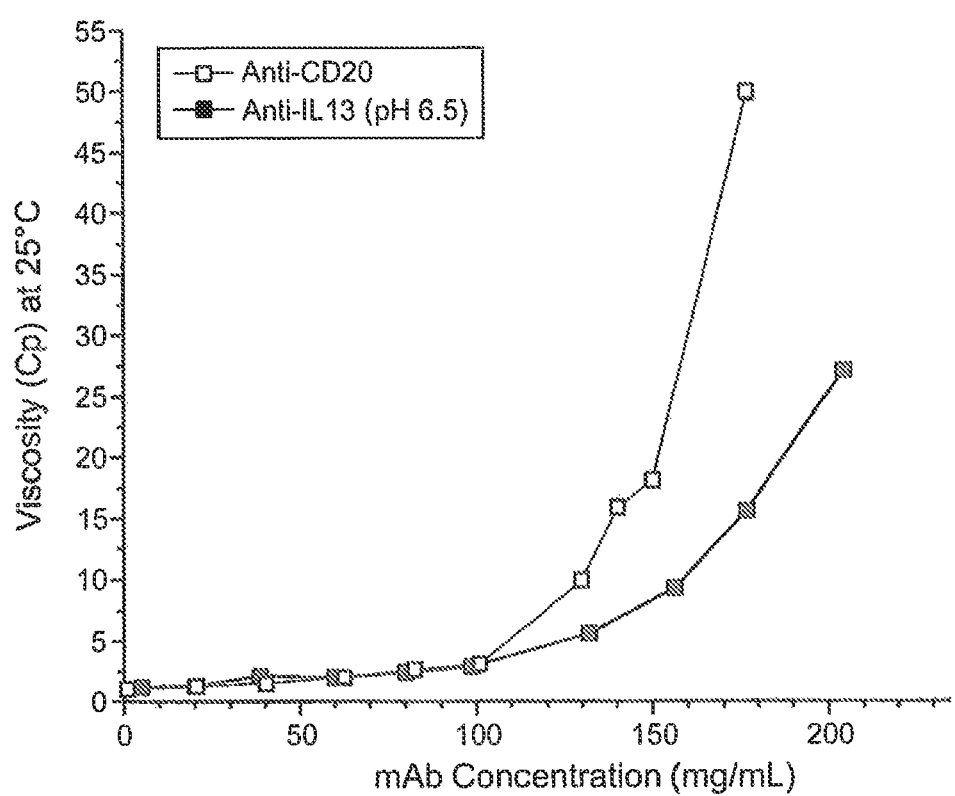
FIG. 20 shows shear viscosity measured for anti-IL13 and anti-CD20 under respective formulation conditions at 25° C. as described in Example 1.

Both anti-IL13 and anti-CD20 showed comparable levels of turbidity caused by attractive colloidal interactions and mAb self association as shown in FIG. 19. Surprisingly, such attractive colloidal interactions did not manifest as high viscosities (e.g., >15 eP at 150 mg/mL) or rheological problems with the formulation for anti-IL13 antibody as shown in FIG. 20. The colloidal interactions for anti-CD20 antibody, however, did have an effect on solution rheology, resulting not only in solution opalescence (FIG. 8) but also high viscosities of >15 cP at 25° C. and 150 mg/mL (FIG. 20).

Long Term Physical, Chemical, and Potency Stability

To test long term stability and potency, anti-IL13 antibody was formulated at 125 mg/mL in 20 mM histidine acetate pH 5.7, 175 mM sucrose and 0.3 mg/mL polysorbate 20 and then subjected to various storage conditions. Vials were stored at either 5° C. or 25° C. for the number of weeks shown in Table 3 (up to 156 weeks at 5° C. and up to 26 weeks at 25° C.). At each time point as indicated in Table 3, samples were analyzed for color appearance and clarity (CAC), pH, and the indicated chemical or physical stability measurement. In addition, biological activity (potency) was also assessed at each time point. As indicated by the data shown in Table 3, the anti-IL13 antibody formulated at 125 mg/mL in 20 mM histidine acetate pH 5.7, 175 mM sucrose and 0.3 mg/mL polysorbate 20 maintained potency and demonstrated good chemical and physical stability at 5° C. for the entire 156 weeks (three years) and at 25° C. for the entire 26 weeks. These data confirm that this formulation maintains the desired chemical, physical and potency attributes of the anti-IL13 antibody for an extended period of time.

TABLE 3

Stability and conditions used to determine long term physical, chemical, and potency stability of anti-IL13 antibody.

| Storage | | | | SEC | icIEF | CE-SDS | | | |
| --- | --- | --- | --- | --- | --- | --- | --- | --- | --- |
| Temp (° C.) | Time (Weeks) | Visual CAC | pH | % Monomer | % Main Peak | % Main Peak | Strength (mg/mL) | Osmolality (mOsm/kg) | Potency (% Specific Activity) |
| −70 T = 0 | 0 | SY, LIQ, SOPL | 5.6 | 99.5 | 72 | 98 | 119 | 267 | 101 |
| 5 | 4 | SY, LIQ, SOPL | 5.6 | 99.5 | 74 | 98 | 128 | 268 | 98 |
| | 8 | SY, LIQ, SOPL | 5.6 | 99.5 | 74 | 98 | 124 | 270 | NT |
| | 12 | SY, LIQ, SOPL | 5.6 | 99.5 | 74 | 98 | 125 | 265 | 98 |
| | 26 | SY, LIQ, SOPL | 5.8 | 99.3 | 73 | 98 | 125 | 264 | 99 |
| | 39 | SY, LIQ, SOPL | 5.8 | 99.4 | 74 | 98 | 123 | 265 | 95 |
| | 52 | SY, LIQ, SOPL | 5.7 | 99.3 | 72 | 98 | 122 | 269 | 102 |
| | 78 | SY, LIQ, SOPL | 5.7 | 99.2 | 72 | 98 | 125 | 266 | 95 |
| | 104 | SY, LIQ, SOPL | 5.7 | 99.1 | 73 | 98 | 124 | 275 | 100 |
| | 130 | SY, LIQ, SOPL | 5.8 | 99.3 | 72 | 98 | 124 | 273 | 93* |
| | 156 | SY, LIQ, SOPL | 5.8 | 99.1 | 71 | 98 | 125 | 268 | 94 |
| 25 | 1 | SY, LIQ, SOPL | 5.6 | 99.5 | 71 | 98 | 125 | 264 | NT |
| | 2 | SY, LIQ, SOPL | 5.7 | 99.4 | 72 | 98 | 124 | 265 | NT |
| | 4 | SY, LIQ, SOPL | 5.7 | 99.2 | 71 | 97 | 123 | 264 | 102 |
| | 8 | SY, LIQ, SOPL | 5.7 | 99.1 | 68 | 97 | 125 | 268 | 98 |
| | 12 | SY, LIQ, SOPL | 5.7 | 99.0 | 62 | 97 | 123 | 270 | 94 |
| | 26 | SY, LIQ, SOPL | 5.8 | 98.7 | 57 | 96 | 129 | 268 | 91 |

CAC: Color Appearance and Clarity
SY = Slightly Yellow
LIQ = Liquid
SOPL = Slightly Opalescent Conclusions We have shown that anti-IL13 antibody has been successfully formulated at pH and solution conditions with excipients that promote both the long term chemical and physical stability and maintain potency. Specifically, that formulation comprised antibody at concentrations of 100 mg/mL and above, including 3.25 mg/mL and 150 mg/mL, in 20 mM histidine acetate pH5.7, 175 mM sucrose and 0.3 mg/mL polysorbate 20. Surprisingly, we found that the formulation had a desirable viscosity profile of <15 cP at 25° C. Such a viscosity profile is desirable for manufacturability and also for ease of administration e.g., for subcutaneous injection where a high concentration of drug product in a small volume is optimal for several reasons including patient comfort and compliance. We observed that other antibodies in the same or similar formulation had an undesirable viscosity profile of >15 cP at 25° C., which highlights the unpredictability of the viscosity profile for anti-IL13 antibody formulations.

In addition, two often used criteria for protein formulation selection include thermal stability and colloidal stability (See Chi et al., Protein Science 12(5):903-913 (2003); Chi et al., Pharmaceutical Research 20(9); 1325-1336 (2003)). Thermal analysis of unfolding temperatures of anti-IL13 antibody solutions suggested that the physical stability at conditions pH 5.4-6.0 would not be optimal for physical stability of the antibody formulation. Colloidal stability analysis of anti-IL13 antibody solutions also suggested that the formulation conditions in the pH range 5.5-6.5 would be least desirable to maintain low aggregation rates. Yet, surprisingly, as shown by the data presented here, anti-IL13 antibody formulated at pH 5.7 demonstrated good physical stability over an extended period of time at 5° C. and also under accelerated conditions. It was also surprising that product stability under these conditions was superior to that observed at higher pHs, both physically and chemically, even though there was lower thermal melting transitions and colloidal stability. While the formulated anti-IL13 antibody solution appearance (and turbidity) was more opalescent in the selected formulation conditions than in certain unselected conditions, the molecular properties and formulation composition maintained optimal stability under both real time and accelerated storage conditions, maintained potency, and provided the desired solution rheological properties for delivery of high concentrations of drug product in a small volume.

Subcutaneous Administration Device

A subcutaneous administration device comprising a pre-filled syringe with needle, a plunger with plunger stopper, a needle shield and a needle safety device for administration of the anti-IL13 formulation described above was selected by evaluating a variety of commercially-available components. For example, the components evaluated included glass cane, formed syringes with staked-in needle, plungers and plunger stoppers, rigid needle shields and needle safety devices.

The various components were evaluated in various combinations according to methods known to one skilled in the art for the effects on formulation properties including, but not limited to, stability, and other considerations such as patient comfort and convenience, which includes factors such as the impact of needle gauge and internal needle diameter on injection time and glide forces when the formulation has certain viscosities as described herein. These studies led us to select as an optimal subcutaneous administration device for the administration of lebrikizumab formulated at high concentration as described herein a prefilled 1.0 mL low tungsten borosilicate glass (type I) syringe and a stainless steel 5-bevel 27 G ½ inch thin-wall staked-in needle with a rigid needle shield comprising FM27/0 (Daetwyler) and a rigid polypropylene shield. In addition, the plunger rod comprised a rubber plunger stopper comprising 4023/50 rubber and FluroTec® ethylene-tetrafluoroethylene (ETFE) coating (West Pharmaceutical Services, Inc.). The subcutaneous administration device also comprised a needle safety device, Ultrasafe Passive® Needle Guard X100L (Safety Syringes, Inc.). The subcutaneous administration device detailed above is referred to below as a staked-in needle prefilled syringe or "SIN PFS."

To demonstrate comparable stability of the lebrikizumab drug product in a vial to the selected SIN PFS, we evaluated GMP drug substance hand-filled into 2 cc vials or 1 mL SIN PFS at 40° C./ambient relative humidity. We assessed degradation rates as characterized by changes in the monomer by size exclusion chromatography (SEC) as well as changes in percent main peak by imaged capillary isoelectric focusing (ICIEF) and capillary electrophoresis sodium dodecyl sulfate (CE-SDS).

These studies revealed that after storage at 40° C. for 4 weeks, there were no significant differences in the decrease in monomer as measured by SEC between vials and SIN PFS (each showing 0.6%-0.9% decrease) or in the decrease in percent main peak (each showing 18-21% decrease as measured by ICIEF and 0.9%-1.5% decrease as measured by CE-SDS). In addition, the chromatographic profiles were comparable to each other and no new peaks were observed in the SIN PFS samples compared to the vial samples.

There were slight differences in degradation rates (0.5%-0.6% increase in high molecular weight species for the vial vs. 0.8% increase in high molecular weight species for the SIN PFS after 4 weeks at 40° C.). This slight difference was considered unlikely to affect product quality during real time storage.

Accordingly, we conclude that the data described above show that the stability of high concentration lebrikizumab drag product formulated as described above in vials is comparable to that in the selected SIN PFS described above.

CERTAIN REFERENCES

Akers, M. J. et al. (2002) "Formulation Development of Protein Dosage Forms", Development and Manufacture of Protein Pharmaceuticals, pgs. 47-127.

Bettelheim, F. A. and E. L. Siew (1983). "Effect of change in concentration upon lens turbidity as predicted by the random fluctuation theory." *Biophysical Journal* 41(1): 29-33.

Burckbuchler, V.; Mckhioufi, G.; Gitcau, A. P.; Grossiord, J. L.; Huille, S.: Agnely, F. *Eur J Pharm Biopharm* 2010, 76, 351.

Chi, E. Y., S. Krishnan, et al. (2003). "Roles of conformational stability and colloidal stability in the aggregation of recombinant human granulocyte colony-stimulating factor." *Protein Science* 12(5): 903-913.

Chi, E. Y., S. Krishnan, et al. (2003), "Physical stability of proteins in aqueous solution: Mechanism and driving forces in normative protein aggregation," *Pharmaceutical Research* 20(9): 1325-1336.

Development and Optimization of Protein Formulation DSC Application Note, available at www(dot)microcalorimetry(dot)com (Oct. 31, 2011).

Goldberg, D. S. et al. (April 2011). "Formulation Development of Therapeutic Monoclonal Antibodies Using High-Throughput Fluorescence and Static Light Scattering Techniques: Roll of Conformational and Colloidal Stability", Journal of Pharm. Sciences, 100, (4): pgs. 1306-1315.

Jezek, J.; Rides, M.; Derham, B.; Moore, J.; Cerasoli, E.; Simler, R.; Perez-Ramirez, B. *Advanced Drug Delivery Reviews* 2011, 63, 1107.

Le Brun, V. et al. (2010): "A critical evaluation of self-interaction chromatography as a predictive tool for the assessment of protein-protein interactions in protein formulation development: A case study of a therapeutic monoclonal antibody", European Journal of Pharmaceutics and Biopharmaceutics, 75, pgs. 16-25.

Mason, B. D. et al. (2011). "Opalescence of an IgG2 Monoclonal Antibody Solution as it Relates to Liquid-Liquid Phase Separation", Journal of Pharm, Sciences, 100, pgs. 4587-4596.

Minton, A. P. (2007). "The effective hard particle model provides a simple, robust, and broadly applicable description of nonideal behavior in concentrated solutions of bovine serum albumin and other nonassociating proteins," *J Pharm Sci* 96(12): 3466-9.

Minton, A. P. (2007). "Static light Scattering from Concentrated Protein Solutions, I: General Theory for Protein Mixtures and Application to Self-Associating Proteins." *Biophysical Journal* 93(4): 1321-1328.

Nishi, H.; Miyajima, M.; Wakiyama, N.; Kubota, K.; Hasegawa, J.; Uchiyama, S.; Fukui, K. *J Biosci Bioeng* 2011, 112, 326.

Nishi, H.; Miyajima, M.; Nakagami, H.; Noda, M.; Uchiyama, S.; Fukui, K. *Pharmaceutical Research* 2010, 27, 1348.

Saito, S.; Hasegawa, J.; Kobayashi, N.; Kishi, N.; Uchiyama, S.; Fukui, K. *Pharm Res* 2012, 29, 397.

Salinas, B. A. et al, (January 2010), "Understanding and Modulating Opalescence and Viscosity in a Monoclonal Antibody Formulation", Journal of Pharm. Sciences, 99 (1): pgs. 82-93.

Saluja, A.; Badkar, A. V.; Zeng, D. L.; Nema, S.; Kalonia, D. S. *Journal of Pharmaceutical Sciences* 2006, 95, 1967.

Scherer, T. M., J. Liu, et al. (2010). "Intermolecular Interactions of IgG1 Monoclonal Antibodies at High Concentrations Characterized by Light Scattering." *The Journal of Physical Chemistry B* 114(40): 12948-12957.

Sukumar, M. et al. (July 2004): "Opalescent Appearance of an IgG1 Antibody at High Concentrations and Its Relationship to Noncovalent Association", Pharm. Research, 21 (7) pgs. 1087-1093.

Volkin, D. B, et al. (2002) "Preformulation Studies as an Essential Guide to Formulation Development and Manufacture of Protein Pharmaceuticals", Development and Manufacture of Protein Pharmaceuticals, 14, 1-46.

Xia, J. Z., T. Aerts, et al. (1994). "Light scattering by bovine alpha-crystallin proteins in solution: hydrodynamic structure and interparticle interaction." *Biophysical Journal* 66(3_Pt_1): 861-872.

Xia, J, Z., Q. Wang, S. Tatarkova, T, Aerts, J. Clauwaert (1996). "Structural basis of eye lens transparency: light scattering by concentrated solutions of bovine alpha-crystallin proteins" *Biophysical Journal* 71(5): 2815-2822.

Yadav, S, J. Liu, et al. (2009). "Specific interactions in high concentration antibody solutions resulting in high viscosity." *J Pharm Sci.*

Yadav, S.; Shire, S. I.; Kalonia, D. S. *Journal of Pharmaceutical Sciences* 2010, 99, 4812.

Yadav, S.; Sreedhara, A.; Kanai, S.; Liu, J.; Lien, S.; Lowman, H.; Kalonia, D. S.; Shire, S. J. *Pharmaceutical Research* 2011, 28, 1750.

Yadav, S.; Liu, J.; Shire, S. J.; Kalonia, D. S. *Journal of Pharmaceutical Sciences* 2010, 99, 1152.

Yadav, S.; Shire, S. J.; Kalonia, D. S. *Journal of Pharmaceutical Sciences* 2012, 101, 998.

Yadav, S.; Shire, S. J.; Kalonia, D. S. *Pharmaceutical Research* 2011, 28, 1973.

---

What is claimed is:

1. A method of administering subcutaneously a formulation, wherein the formulation is within an article of manufacture comprising the formulation and a subcutaneous administration device; wherein the formulation comprises an anti-IL13 antibody, wherein the concentration of the anti-IL-13 antibody in the formulation is at least 100 mg/mL and the viscosity of the formulation is less than 15 centipoise (cP) at 25° C., wherein the formulation comprises a histidine acetate buffer, pH 5.4 to 6.0, and the histidine acetate concentration in the buffer is between 5 mM and 40 mM, and wherein the anti-IL-13 antibody is an IgG4 antibody and comprises three heavy chain CDRs, CDR-H1 having the amino acid sequence of SEQ ID NO: 1, CDR-H2 having the amino acid sequence of SEQ ID NO: 2, and CDR-H3 having the amino acid sequence of SEQ ID NO: 3, and three light chain CDRs, CDR-L1 having the amino acid sequence of SEQ ID NO: 4, CDR-L2 having the amino acid sequence of SEQ ID NO: 5, and CDR-L3 having the amino acid sequence of SEQ ID NO: 6.

2. The method of claim 1, wherein the formulation has extended stability.

3. The method of claim 1, wherein the formulation comprises 20 mM histidine acetate buffer, pH 5.7, 175 mM sucrose, and 0.03% polysorbate 20, wherein the concentration of the anti-IL-13 antibody in the formulation is 125 mg/mL.

4. The method of claim 3, wherein the subcutaneous administration device comprises a prefilled syringe.

5. The method of claim 3, wherein the subcutaneous administration device comprises an autoinjector.

6. The method of claim 3, wherein the subcutaneous administration device comprises an injector pen.

7. The method of claim 1, wherein the formulation comprises 20 mM histidine acetate buffer, pH 5.7, 175 mM sucrose, and 0.03% polysorbate 20, wherein the concentration of the anti-IL-13 antibody in the formulation is 150 mg/mL.

8. The method of claim 7, wherein the subcutaneous administration device comprises a prefilled syringe.

9. The method of claim 8, wherein the syringe comprises low tungsten borosilicate glass.

10. The method of claim 7, wherein the subcutaneous administration device comprises an autoinjector.

11. The method of claim 7, wherein the subcutaneous administration device comprises an injector pen.

12. The method of claim 1, wherein the subcutaneous administration device comprises a prefilled syringe.

13. The method of claim 12, wherein the syringe comprises low tungsten borosilicate glass.

14. The method of claim 1, wherein the subcutaneous administration device comprises an autoinjector.

15. The method of claim 1, wherein the subcutaneous administration device comprises an injector pen.

16. The method of claim 1, wherein the anti-IL13 antibody comprises a VH having the amino acid sequence of SEQ ID NO: 7 or 8, and a VL having the amino acid sequence of SEQ ID NO: 9.

17. The method of claim 1, wherein the anti-IL13 antibody comprises a heavy chain having the amino acid sequence of any one of SEQ ID NO: 10, 11, 12, or 13, and a light chain having the amino acid sequence of SEQ ID NO: 14.

18. The method of claim 1, wherein the concentration of the anti-IL-13 antibody in the formulation is between 100 mg/mL and 150 mg/mL.

* * * * *

SEQUENCE LISTING

```
<160> NUMBER OF SEQ ID NOS: 14

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Tyr Ser Val Asn
1               5

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Met Ile Trp Gly Asp Gly Lys Ile Val Tyr Asn Ser Ala Leu Lys Ser
1               5                   10                  15

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Gly Tyr Tyr Pro Tyr Ala Met Asp Asn
1               5                   10
```

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Lys Ser Val Asp Ser Tyr Gly Asn Ser Phe Met His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Leu Ala Ser Asn Leu Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Asn Asn Glu Asp Pro Arg Thr
1               5

<210> SEQ ID NO 7
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Val Thr Leu Arg Glu Ser Gly Pro Ala Leu Val Lys Pro Thr Gln Thr
1               5                   10                  15

Leu Thr Leu Thr Cys Thr Val Ser Gly Phe Ser Leu Ser Ala Tyr Ser
            20                  25                  30

Val Asn Trp Ile Arg Gln Pro Pro Gly Lys Ala Leu Glu Trp Leu Ala
        35                  40                  45

Met Ile Trp Gly Asp Gly Lys Ile Val Tyr Asn Ser Ala Leu Lys Ser
    50                  55                  60

Arg Leu Thr Ile Ser Lys Asp Thr Ser Lys Asn Gln Val Val Leu Thr
65                  70                  75                  80

Met Thr Asn Met Asp Pro Val Asp Thr Ala Thr Tyr Tyr Cys Ala Gly
                85                  90                  95

Asp Gly Tyr Tyr Pro Tyr Ala Met Asp Asn Trp Gly Gln Gly Ser Leu
            100                 105                 110

Val Thr Val Ser Ser
        115

-continued

```
<210> SEQ ID NO 8
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Gly Asp Gly Tyr Tyr Pro Tyr Ala Met Asp Asn Trp Gly Gln Gly Ser
            100                 105                 110

Leu Val Thr Val Ser Ser
        115

<210> SEQ ID NO 9
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Val Met Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

Glu Asp Pro Arg Thr Phe Gly Gly Gly Thr Lys Val Glu Ile Lys Arg
            100                 105                 110

<210> SEQ ID NO 10
<211> LENGTH: 443
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Val Thr Leu Arg Glu Ser Gly Pro Ala Leu Val Lys Pro Thr Gln Thr
1               5                   10                  15
```

```
Leu Thr Leu Thr Cys Thr Val Ser Gly Phe Ser Leu Ser Ala Tyr Ser
            20                  25                  30

Val Asn Trp Ile Arg Gln Pro Pro Gly Lys Ala Leu Glu Trp Leu Ala
        35                  40                  45

Met Ile Trp Gly Asp Gly Lys Ile Val Tyr Asn Ser Ala Leu Lys Ser
    50                  55                  60

Arg Leu Thr Ile Ser Lys Asp Thr Ser Lys Asn Gln Val Val Leu Thr
65                  70                  75                  80

Met Thr Asn Met Asp Pro Val Asp Thr Ala Thr Tyr Tyr Cys Ala Gly
                85                  90                  95

Asp Gly Tyr Tyr Pro Tyr Ala Met Asp Asn Trp Gly Gln Gly Ser Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430
```

-continued

```
Tyr Thr Gln Lys Ser Leu Ser Leu Ser Leu Gly
            435                 440

<210> SEQ ID NO 11
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Gly Asp Gly Tyr Tyr Pro Tyr Ala Met Asp Asn Trp Gly Gln Gly Ser
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350
```

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
        435                 440

<210> SEQ ID NO 12
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Val Thr Leu Arg Glu Ser Gly Pro Ala Leu Val Lys Pro Thr Gln Thr
1               5                   10                  15

Leu Thr Leu Thr Cys Thr Val Ser Gly Phe Ser Leu Ser Ala Tyr Ser
            20                  25                  30

Val Asn Trp Ile Arg Gln Pro Pro Gly Lys Ala Leu Glu Trp Leu Ala
        35                  40                  45

Met Ile Trp Gly Asp Gly Lys Ile Val Tyr Asn Ser Ala Leu Lys Ser
    50                  55                  60

Arg Leu Thr Ile Ser Lys Asp Thr Ser Lys Asn Gln Val Val Leu Thr
65                  70                  75                  80

Met Thr Asn Met Asp Pro Val Asp Thr Ala Thr Tyr Tyr Cys Ala Gly
            85                  90                  95

Asp Gly Tyr Tyr Pro Tyr Ala Met Asp Asn Trp Gly Gln Gly Ser Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe

```
              260                 265                 270
Asn Trp Tyr Val Asp Gly Val Glu Val His Asn Ala Lys Thr Lys Pro
            275                 280                 285
Arg Glu Glu Gln Phe Asn Ser Thr Tyr Arg Val Val Ser Val Leu Thr
            290                 295                 300
Val Leu His Gln Asp Trp Leu Asn Gly Lys Glu Tyr Lys Cys Lys Val
305                 310                 315                 320
Ser Asn Lys Gly Leu Pro Ser Ser Ile Glu Lys Thr Ile Ser Lys Ala
                325                 330                 335
Lys Gly Gln Pro Arg Glu Pro Gln Val Tyr Thr Leu Pro Pro Ser Gln
                340                 345                 350
Glu Glu Met Thr Lys Asn Gln Val Ser Leu Thr Cys Leu Val Lys Gly
                355                 360                 365
Phe Tyr Pro Ser Asp Ile Ala Val Glu Trp Ser Asn Gly Gln Pro
            370                 375                 380
Glu Asn Asn Tyr Lys Thr Thr Pro Pro Val Leu Asp Ser Asp Gly Ser
385                 390                 395                 400
Phe Phe Leu Tyr Ser Arg Leu Thr Val Asp Lys Ser Arg Trp Gln Glu
                405                 410                 415
Gly Asn Val Phe Ser Cys Ser Val Met His Glu Ala Leu His Asn His
                420                 425                 430
Tyr Thr Gln Lys Ser Leu Ser Leu Ser Leu Gly Lys
            435                 440

<210> SEQ ID NO 13
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Thr Leu Arg Glu Ser Gly Pro Ala Leu Val Lys Pro Thr Gln
1               5                   10                  15
Thr Leu Thr Leu Thr Cys Thr Val Ser Gly Phe Ser Leu Ser Ala Tyr
            20                  25                  30
Ser Val Asn Trp Ile Arg Gln Pro Pro Gly Lys Ala Leu Glu Trp Leu
        35                  40                  45
Ala Met Ile Trp Gly Asp Gly Lys Ile Val Tyr Asn Ser Ala Leu Lys
    50                  55                  60
Ser Arg Leu Thr Ile Ser Lys Asp Thr Ser Lys Asn Gln Val Val Leu
65                  70                  75                  80
Thr Met Thr Asn Met Asp Pro Val Asp Thr Ala Thr Tyr Tyr Cys Ala
                85                  90                  95
Gly Asp Gly Tyr Tyr Pro Tyr Ala Met Asp Asn Trp Gly Gln Gly Ser
            100                 105                 110
Leu Val Thr Val Ser Ser Ala Ser Thr Lys Gly Pro Ser Val Phe Pro
        115                 120                 125
Leu Ala Pro Cys Ser Arg Ser Thr Ser Glu Ser Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
```

-continued

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 14
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Val Met Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95

-continued

```
Glu Asp Pro Arg Thr Phe Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```